(12) United States Patent
Trumper et al.

(10) Patent No.: US 8,669,771 B2
(45) Date of Patent: Mar. 11, 2014

(54) SYSTEM AND METHOD FOR PROVIDING ELECTROMAGNETIC IMAGING THROUGH ELECTROQUASISTATIC SENSING

(75) Inventors: David L. Trumper, Plaistow, NH (US); Jeffrey H. Lang, Sudbury, MA (US); Benjamin L. Cannon, Jeannette, PA (US); Markus Zahn, Lexington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 538 days.

(21) Appl. No.: 12/695,940

(22) Filed: Jan. 28, 2010

(65) Prior Publication Data
US 2010/0194374 A1    Aug. 5, 2010

Related U.S. Application Data

(60) Provisional application No. 61/148,043, filed on Jan. 28, 2009.

(51) Int. Cl.
*G01R 27/26*     (2006.01)

(52) U.S. Cl.
USPC ............ 324/658; 324/681; 324/683; 324/307

(58) Field of Classification Search
USPC .................................. 324/658, 681, 683, 307
See application file for complete search history.

(56) References Cited

U.S. PATENT DOCUMENTS

| | | | |
|---|---|---|---|
| 4,814,690 A |   | 3/1989 | Melcher et al. |
| 5,963,679 A | * | 10/1999 | Setlak ........................ 382/312 |
| 7,411,390 B2 |   | 8/2008 | Goldfine et al. |
| 2007/0089518 A1 | * | 4/2007 | Ericson et al. .................. 73/649 |
| 2009/0041187 A1 |   | 2/2009 | Peschmann et al. |
| 2010/0253332 A1 |   | 10/2010 | Trumper et al. |

FOREIGN PATENT DOCUMENTS

WO     WO9830921 A2     7/1998

OTHER PUBLICATIONS

Li, et al., "Design of Multi-Chanel Fringing Electric Field Sensors for Imaging-Part I: General Design Principles" IEEE International Symposium on Electrical Insulation, Indianapolis, IN, pp. 406-409; doi=10.1.1.133.9960, Sep. 19-22, 2004, entire document.
Mauer, "An End-effector Based Imaging Proximity Sensor." J. Robotic Systems, vol. 6, No. 3, pp. 301-316, Jun. 1989, p. 312, para [002].
Lanyi, S.; Torok, J.; Rehurek, P.: A Novel Capacitance Microscope, Review of Scientific Instruments, vol. 65, No. 7, pp. 2258-2261, Jul. 1994, American Institute of Physics.

(Continued)

*Primary Examiner* — Vincent Q Nguyen
(74) *Attorney, Agent, or Firm* — Peter A. Nieves; Sheehan Phinney Bass + Green PA

(57) ABSTRACT

A system and method for providing electromagnetic imaging through electroquasistatic sensing contains an electromagnetic sensor for imaging a sample. The electromagnetic sensor contains drive/sense electronics and a pixelated sensor array having an array of capacitive sensor electrodes that source electric fields that interact with the sample, and wherein the electrodes are individually drivable by the drive/sense electronics in a coordinated manner to establish a desired temporal and spatial pattern in which electrical properties of the electrodes are used to generate an image. Other components of the system include a precision motion controller, sensor head and associated electronics, and a computer for performing data acquisition and signal inversion.

25 Claims, 38 Drawing Sheets

(56) References Cited

OTHER PUBLICATIONS

Dreyer, M.: Wiesendanger, R.: Scanning Capacitance Microscopy and Spectroscopy Applied to Local Charge Modificatiions and Characterization of Nitride-Oxide-Silicon Heterostructures, Applied Physics A. 61, pp. 357-362, 1995, Springer-Verlag 1995.
Imtiaz, Atif; Anlage, Steven M.: A Novel STM-Assisted Microwave Microscope with Capacitance and Loss Imaging Capability, Ultramicroscopy 94 (2003) pp. 209-216, Elsevier Science B.V.
Oliver, Rachel A.: Advances in AFM for the Electrical Characterization of Semiconductors, Reports on Progress in Physics, 71 (Jun. 20, 2008) 076501 (37 pages) IOP Publishing Ltd., printed in the UK.
Nakagiri, Nobuyuki; Yamamoto, Takuma; Sugimura, Hiroyuki; Suzuki, Yoshihiko; Miyashita, Masayuki; Wantanabe, Shunji: Application of Scanning Capacitance Microscopy to Semiconductor Devices, Nanotechnology 8 (1997), A32-A37, IOP Publishing Ltd., printed in the UK.
Huang, Y; Williams, C.C.: Capacitance-Voltage Measurement and Modeling on a Nanometer Scale by Scanning C-V Microscopy, Journal of Vacuum Science & Technology, B 12(1), Jan./Feb. 1994 pp. 369-372, American Vacuum Society.
Sheiretov, Y.; Zahn, M.: Dielectrometry Measurements of Moisture Dynamics in Oil-Impregnated Pressboard, IEEE Transactions on Dielectrics and Electrical Insulation, vol. 2, No. 3, Jun. 1995, pp. 329-351.
Harigai, Takakiyo; Tanaka, Daisuke; Kakemoto, Hirofumi; Wada, Satoshi; Tsurumi, Takaaki: Dielectric Properties of BaTiO3/SrTiO3 Superlattices Measured with Interdigital Electrodes and Electromagnetic Field Analysis, Journal of Applied Physics, vol. 94, No. 12, Dec. 15, 2003, pp. 7923-7925, American Institute of Physics.
Martin, Yves; Abraham, David W.; Wickramasinghe, H. Kumar; High-Resolution Capacitance Measurement and Potentiometry by Force Microscopy, Applied Phyics Letters, 52, (13), Mar. 28, 1988, pp. 1103-1105, American Institute of Physics.
Matey, J.R.: Blanc, J.: Scanning Capacitance Microscopy, Journal of Applied Physics 57 (5), Mar. 1, 1985, pp. 1437-1444, American Institute of Physics.
Bugg, C D; King, P J: Scanning Capacitance Microscopy, Journal of Physics E: Scientific Instruments, 21 (1988) pp. 147-151, IOP Publishing Ltd., printed in the UK.
Mackel, R.; Baumgartner, H.; Ren, J.: The Scanning Kelvin Microscope, Review of Scientific Instruments 64 (3), Mar. 1993, pp. 694-699, American Institute of Physics.
Asami, Koji: The Scanning Dielectric Microscope, Measurement Science and Technology, 5 (1994) pp. 589-592, IOP Publishing Ltd., printed in the UK.

Kopanski, J.J.; Marchiando, J.F.; Lowney, J.R.: Scanning Capacitance Microscopy Measurements and Modeling: Progress Towards Dopant Profiling of Silicon, Journal of Vacuum Science & Technology B 14(1), Jan./Feb. 1996, pp. 242-247.
Lanyi, S.; Torok, J.; Rehurek, P.: Imaging Conducting Surfaces and Dielectric Films by a Scanning Capacitance Microscope, Journal of Vacuum Science & Technology B 14(2), Mar./Apr. 1996, pp. 892-896, American Vacuum Society.
Goto, Kazuya; Hane, Kazuhiro: Tip-Sample Capacitance in Capacitance Microscopy of Dielectric Films, Journal of Applied Physics, vol. 84, No. 8, Oct. 15, 1998, pp. 4043-4048, American Institute of Physics.
Williams, C.C.: Two-Dimensional Dopant Profiling by Scanning Capacitance Microscopy, Annual Review of Materials Science, (1999), vol. 29, pp. 471-504.
Schlicker, D., Washabaugh, A.; Shay, I.; Goldfine, N.: Inductive and Capactive Array Imaging of Buried Objects, 16th World Conference on Nondestructive Testing, Montreal, Canada Aug. 30-Sep. 3, 2004.
Mamishev, Alexander V.; Sundara-Rajan, Kishore; Yang, Fumin; Du, Yanqing; Zahn, Markus: Interdigital Sensors and Transducers, Proceedings of the IEEE, vol. 92, No. 5, May 2004, pp. 808-845.
Williams, C.C.; Slinkman, J.; Hough, W.P.; Wickramasinghe, H.K.: Lateral Dopant Profiling on a 100 nm Scale by Scanning Capacitance, Journal of Vacuum Science & Technology A 8 (2), Mar./Apr. 1990, American Vacuum Society.
Lesieutre, B.C.; Mamishev, A.V.; Y. Du; E. Keskiner; M. Zahn; G.C. Verghese; Forward and Inverse Parameter Estimation Algorithms of Interdigital Dielectrometry Sensors; IEEE Transactions of Dielectrics and Electric Insulation, vol. 8, No. 4, Aug. 2001, pp. 577-588.
Adrian M. Kummer and Andreas Hierlemann; Configurable Electrodes for Capacitive-Type Sensors and Chemical Sensors; IEEE Sensors Journal, vol. 6, No. 1, Feb. 2006, pp. 3-10.
C.C. Williams, J. Slinkman, W.P. Hough and H.K. Wickramasinghe; Lateral Dopant Profiling with 200 NM Resolution by Scanning Capacitance, Appl. Phys. Lett. 55(16) Oct. 16, 1989, pp. 1662-1664.
C.C. Williams, W.P. Hough, and S.A. Rishton, Scanning Capacitance Microscopy on a 25 NM Scale; Appl. Phys. Lett. 55, Jul. 10, 1989, p. 203-205.
Massood Tabib-Azar, Yaqiang Wang, Design and Fabrication of Scanning Near-field Microwave Proves Compatible with Atomic Force Microscopy to Image Embedded Nanostructures; IEEE Transactions on Microwave Theory and Techniques, vol. 52, No. 3, Mar. 2004, pp. 971-979.
Hongze Liu, Aaron Hawkins, Stephen Schultz, Travis E. Oliphant: Non-contact Scanning Electrical Impedance Imaging; Proceedings of the 26th Annual International Conference of the IEEE EMBS, San Francisco, CA, Sep. 1-5, 2004, pp. 1306-1309.

* cited by examiner

Electrode #
Spatial Dimension

SYSTEM AND METHOD FOR PROVIDING ELECTROMAGNETIC IMAGING THROUGH ELECTROQUASISTATIC SENSING

CROSS-REFERENCE TO RELATED APPLICATIONS

The present application claims priority to co-pending U.S. Provisional Application entitled, "SYSTEM AND METHOD FOR PROVIDING ELECTROMAGNETIC IMAGING," having patent application Ser. No. 61/148,043, filed Jan. 28, 2009, which is entirely incorporated herein by reference.

FIELD OF THE INVENTION

The present invention is generally related to imaging technologies, and more particularly is related to imaging technologies capable of measurements in the near-surface-volume of a material.

BACKGROUND OF THE INVENTION

The statements in this section merely provide background information related to the present disclosure and may not constitute prior art.

Methods of measuring a sample are desirable. For example, it is desirable to be able to measure the geometry of features on a sample with resolution on the order of micrometers or nanometers, for instance in the case of semiconductor integrated circuits and photomasks, microelectromechanical devices, and other microstructures. Additionally, surface and subsurface objects, defects, and anomalies in a sample or device may result in detrimental effects when the device is used. As an example, it is desirable to be able to detect unwanted contamination particles present on photoreticles (and their protective pellicles) used in the mass production of integrated circuits as well as the detection of other defects that might arise during fabrication of these integrated circuits. Other examples of the usefulness of measuring samples in the integrated circuit industry include the evaluation of buried conductor traces in multiple insulating layers and the characterization/imaging of high aspect ratio isolation trenches that prevent current leakage between adjacent integrated circuit (IC) components. Additionally, it may be desirable to measure magnetic and electric field patterns created in the vicinity of operating integrated circuits.

In the early 1980's Binnig and Rohrer developed the scanning tunneling microscope (STM). In this same year, Binnig, Quate, and Gerber invented the atomic force microscope (AFM), which is built on the principles of the STM. In general, an AFM works by monitoring forces between a sharp probe tip and a sample as it is precision scanned over the surface of the sample. In 1984, Matey and Blanc of RCA Laboratories invented scanning capacitive microscopy (SCM) where they utilized pre-developed instrumentation and pickup circuitry from the RCA capacitive electronic disc (CED) VideoDisc player. SCM is similar to AFM but specifically targets changes in capacitance between the probe tip and the surface, and for this reason, SCM is also referred to as scanning probe capacitance imaging. These inventions in the 1980's have spawned a great deal of research into the use of scanning probe microscopy as a means for high-resolution imaging of objects at both macroscopic and microscopic scales.

In the most general sense, an SCM works by scanning an electrically conducting probe over the surface of a sample. FIG. 1, which is taken from Applied Physics, by J. R. Matey and J. Blanc, Volume 57, page 1437 (1985), illustrates the basic geometry of a prior art SCM probe head 10 over a sample 14. As shown by FIG. 1, the SCM probe head 10 houses a sharp tip electrode 12, which is scanned over the surface of the sample 14.

An image is created by monitoring local changes in capacitance between the sharp tip electrode 12 and the sample 14 or a conducting surface under the sample 14. This change in capacitance serves as the contrast agent in the generated image. While there have been many different approaches toward improving SCM, primarily with respect to probe shape, pickup circuitry, and image reconstruction, what has remained common amongst groups attempting to develop high-resolution nanometer scale imaging devices via AFM SCM is the use of a single sense electrode. A well-known and well-documented pitfall of the single sense electrode is its inherent lack of ability to shape the electric field to a desired configuration in order to allow selective spatial imaging. While it is possible to raster scan a single probe electrode over a surface with high lateral resolution, such a configuration does not, for example, provide information for characterizing the depth and volume of the sample in desired spatial dimensions. Consequently, the single probe design cannot optimize spatial and depth parameters and resolution, such as depth and width A single probe also does not allow high imaging speed of the area of a surface to be measured.

Magnetic scanning probe microscopes are another technology, analogous to SCM and used to image magnetic properties. Other magnetic sensors are used in the industry to detect fine patterns. For example, the magnetic read head on a hard disk is used to detect very fine magnetic bit patterns on the surface of a hard disk platter. However, arrays of magnetically driven and/or detected sensors have not been used to generate high resolution two-dimensional and three-dimensional images of submicron scale.

Electromagnetic electrode arrays (electroquasistatic, magnetoquasistatic, and electrodynamic) for object detection and mapping have been used in widely different fields implementing various different electrode geometries. Examples include the use of circular electrode rings for the mapping of biological systems inside the ring (commonly referred to as electrical impedance tomography (EIT)), and the use of coplanar, interdigital electrodes for buried object detection and non-destructive testing. Unfortunately, electroquasistatic electrode arrays and magnetoquasistatic coil arrays have not yet been utilized to generate high resolution, two-dimensional and three-dimensional images of sub-micron scale devices, such as, for example, integrated circuit features.

Thus, a heretofore unaddressed need exists in the industry to address the aforementioned deficiencies and inadequacies.

SUMMARY OF THE INVENTION

Embodiments of the present invention provide a system and method for providing electromagnetic imaging through electroquasistatic sensing. Briefly described, in architecture, one embodiment of the system, among others, can be implemented as follows. The system contains an electromagnetic sensor for imaging a sample. The electromagnetic sensor contains drive/sense electronics and a pixelated sensor array having an array of capacitive sensor electrodes that source electric fields that interact with the sample, and wherein the electrodes are individually drivable by the drive/sense electronics in a coordinated manner to establish a desired temporal and spatial pattern in which electrical properties of the electrodes are used to generate an image. Other components of the system include a precision motion controller, sensor head and associated electronics, and a computer for performing data acquisition and signal inversion.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

The present invention provides a system and method for providing electromagnetic imaging through use of an electromagnetic sensor array. The system is also referred to herein as an electromagnetic imager.

Providing high-resolution images of a certain sample is a valuable tool for imaging surface and subsurface features, detecting surface and subsurface objects, detecting defects, and detecting anomalies in a material that would otherwise go unnoticed by other means of inspection. Such items can be located and imaged with the present system and method. Among other things, the system and method is capable of locating objects with sub-micrometer scale resolution. This sub-micron precision, coupled with its high sensitivity to local changes in dielectric permittivity, magnetic permeability, and electric conductivity, allows for imaging of integrated circuits (ICs) and other devices with features in the micrometer to nanometer regime. It should be noted, however, that the present invention is not limited in scale to the nanometer scale. Instead, while the following provides an example of using the present system and method in the nanometer scale, there is no requirement for such a limitation to scale and the example is merely provided for exemplary purposes.

Examples of industry applications that can benefit from the present system and method include, but are not limited to, the detection and imaging of unwanted contamination particles present on photoreticles, and their protective pellicles, used in the mass production of integrated circuits and the detection of other defects that might arise during the fabrication of integrated circuits, the evaluation of buried conductor traces in multiple insulating layers, and the characterization/imaging of high aspect ratio isolation trenches. In addition to imaging IC features and defects with an electrically driven sensor array, a passive implementation of the same sensor array is provided and used for both time and spatial monitoring of electric field and magnetic field signals in the vicinity of an operating circuit. The following provides a detailed description of active and passive sensor use, in addition to computer simulation of results. Of course, there are many other applications for the present system and method, and the embodiments discussed herein.

Figure 1:
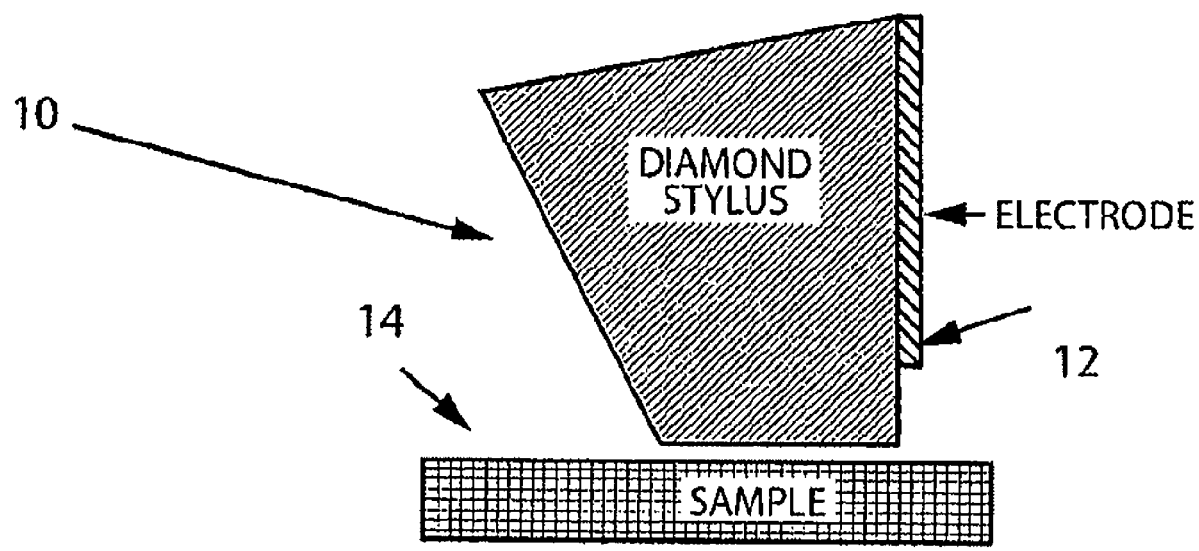
FIG. 1 is a schematic diagram illustrating a prior art probe head housing a sharp tip electrode.
Figure 2:
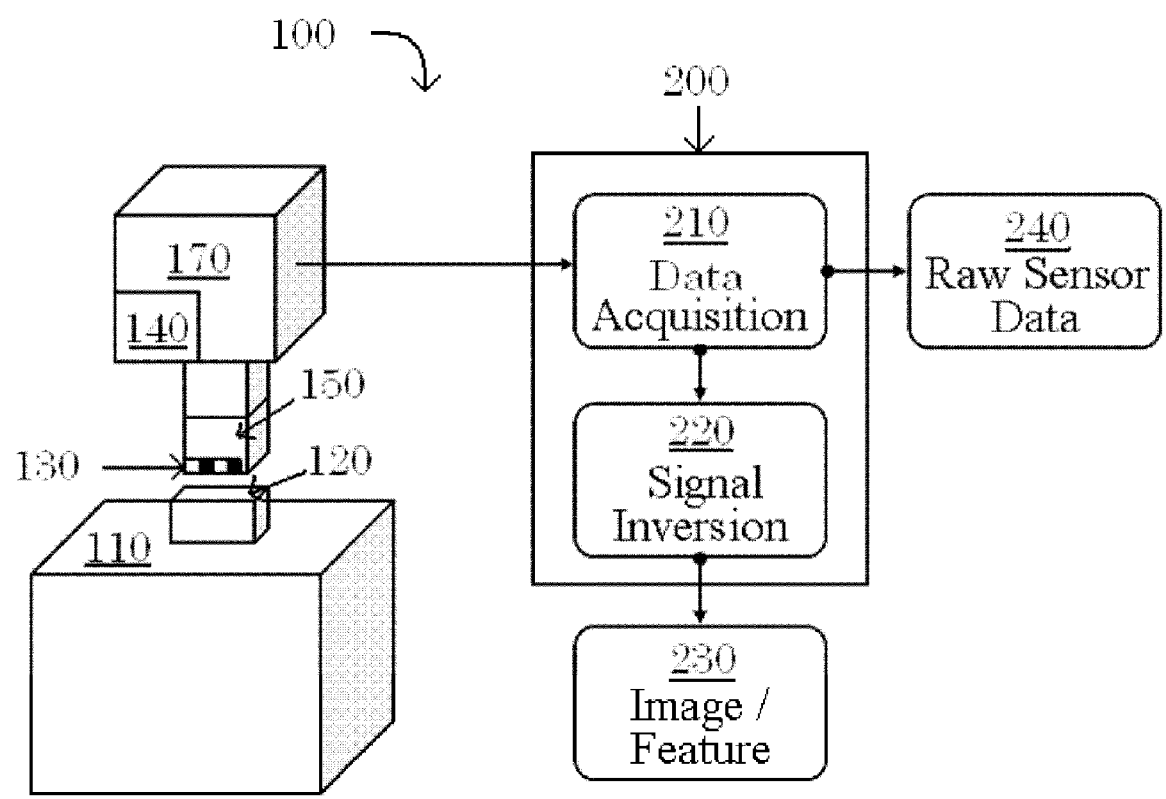
FIG. 2 is a schematic diagram illustrating the present system.

FIG. 2 is a schematic diagram illustrating the system 100 in accordance with a first exemplary embodiment of the invention. As shown by FIG. 2, the system 100 contains a stage 110 upon which a sample 120 rests. The stage 110 is a three-dimensional stage having three orthogonal degrees of freedom (e.g., x-y-z, R-theta-phi, r-phi-z, etc.). The stage 110 is capable of large scale motions with high resolution, although it is not limited to such motions. Large scale scanning/raster-scanning can involve moving the stage and/or the sensor head.

An electromagnetic sensor array 130 is positioned and maintained above the sample 120 a specific distance so as to allow for the array 130 to be used in an active mode and passive mode. The active mode and passive mode of the sensor array 130 is described in detail hereinbelow. In accordance with one embodiment of the invention, features that are imaged by the sensor array 130 are small compared to the sensor array 130.

The sensor array 130 is maintained a very small distance from the surface of the sample 120. As an example, the sensor array 130 may be maintained approximately one-hundred (100) nanometers from the surface of the sample 120. Of course, the sensor array 130 may be maintained a different distance from the surface of the sample 120. Different techniques may be used to maintain this small distance between the sensor array 130 and the sample 120. An example of such a technique may include, but is not limited to, implementing feedback position control via sensing capacitance from the sample 120, sensing currents relative to voltages of electrodes within the sensor array 130, or maintaining an average impedance over the sensor array 130 constant in order to maintain the small distance (height).

The electromagnetic sensor array 130 is connected to drive/sense amplifiers 150, which are, in turn, connected to a sensor head and associated electronics 170. The amplifiers 150 are positioned as close to the sensor array 130 as possible so as not to amplify parasitics/strays. These electronics could include integrated circuitry and/or surface mounted circuitry. The sensor head and electronics 170 may include A/D converters, D/A converters, detectors, mixers, demodulators, feed lines, or other electronics. These electronics, along with the drive/sense amplifiers 150, interface the sensor array 130 and what is sent to a computer 200. In one embodiment, the drive/sense amplifiers and other processing electronics can be integrated within the sensor head itself, using integrated circuit fabrication techniques in concert with microelectromechanical fabrication techniques.

Collectively, the electromagnetic sensor array, drive/sense amplifiers, and sensor head and associated electronics may be referred to as the sensor.

The electromagnetic sensor array 130 can be fundamentally either electric or magnetic in character, assuming that the array size is smaller than the wavelength of light at the chosen frequency of interest. The two sensor arrays are well known to be duals of one another. The electric array contains capacitive electrodes that source electric fields that interact with the sample. The magnetic array contains inductive loops that source magnetic fields that interact with the sample. The important difference here is that the magnetic fields can penetrate conductors that the electric fields would not. Then, the two fields interact differently with the sample, offering different views of its configuration, geometry, and constituent materials. Depending upon the application, one might prefer one embodiment, the other, or both.

Figure 3:
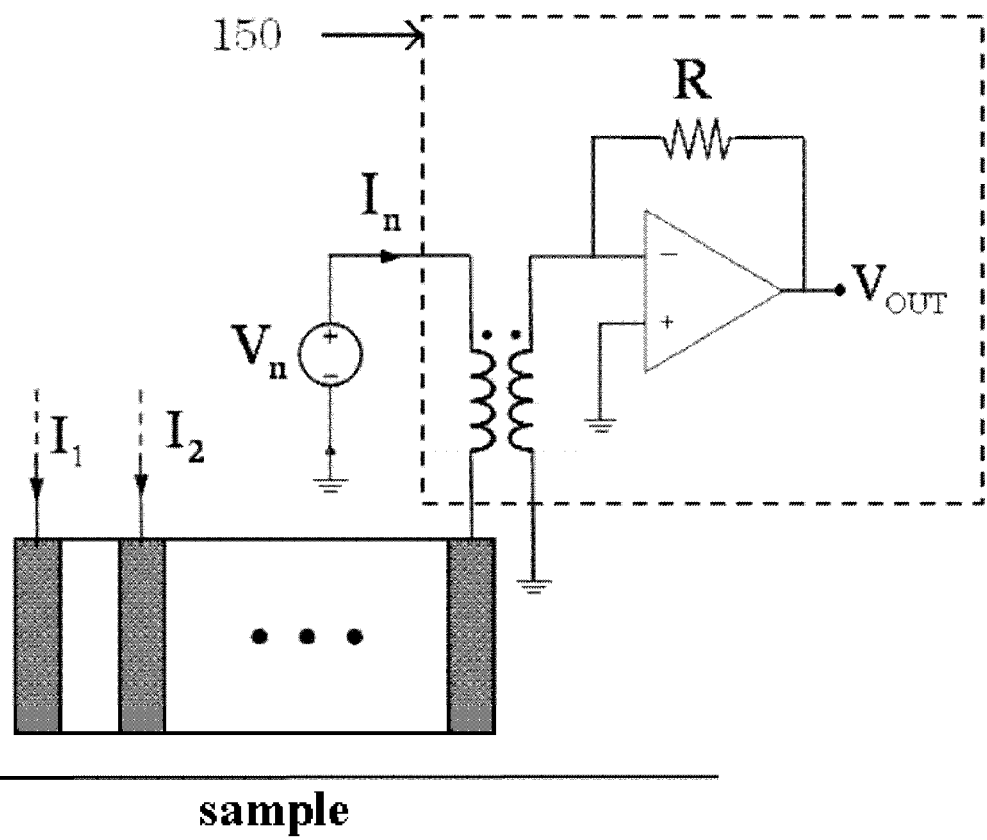
FIG. 3 is a schematic diagram providing an example of a drive/sense amplifier.

FIG. 3 is a schematic diagram providing an example of a drive/sense amplifier 150. It should be noted that the example of FIG. 3 is provided merely for exemplary purposes and is not intended to limit examples of active mode pick-ups that may be used to pickup and measure the current on an electrode. FIG. 3 provides the example of using a transformer and amplifier configuration to pickup and measure the current on an electrode 132. Different operating frequencies may call for different electronics. It should be noted that FIG. 3 is one example of an impedance sensing circuit. Since other impedance sensing methods would be known to one having ordinary skill in the art, the present invention is not intended to be limited to the example of FIG. 3.

Referring back to FIG. 2, a precision motion controller 140 may also be located on the sensor head 170 for ultra-fine vertical and lateral movement of the sensor array 130. It should be noted that in an embodiment having a precision motion controller, collectively, the electromagnetic sensor array, drive/sense amplifiers, precision motion controller, and sensor head and associated electronics may be referred to as the sensor.

The sensor head and electronics 170 are connected to the computer 200. The computer 200 contains several modules for performing specific functionality as required by the present system and method. A first module 210 provides for data acquisition from the sensor head and electronics 170.

A second module 220 of the computer 200 provides signal inversion of data from the sensor array 130. Such signal inversion may be provided by a signal inversion algorithm. Signal inversion is described in detail hereinbelow. The use of signal inversion methods allows for the generation of images, feature parameters, material properties, and other results.

The computer 200 may also have input and output devices 230 connected thereto. Examples of output devices may include, for example, a monitor or printer. In addition, examples of input devices may include, for example, a keyboard, mouse, microphone, and of course, the data from the sensor array 130. Further, input and output devices 230 may include devices that communicate both as inputs and outputs, for instance, but not limited to, a modulator/demodulator (modem; for accessing another device, system, or network), a radio frequency (RF) or other transceiver, a telephonic interface, a bridge, or a router.

It should be noted that an output of the computer 200 may be raw sensor data 240 that may be transmitted to a remote location for post-processing. Alternatively, the computer 200 may contain logic therein for allowing the processing of the raw data therein.

Figure 4A:
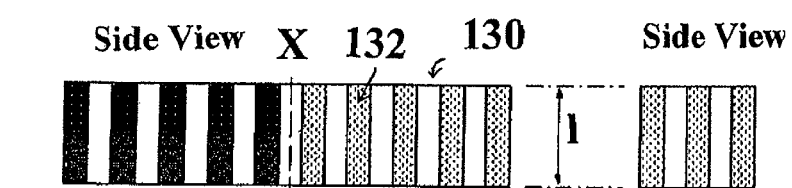
FIG. 4A, FIG. 4B, and FIG. 4C provide a side view, bottom view, and isometric view, respectively, of a sensor array of FIG. 2.
Figure 4B:
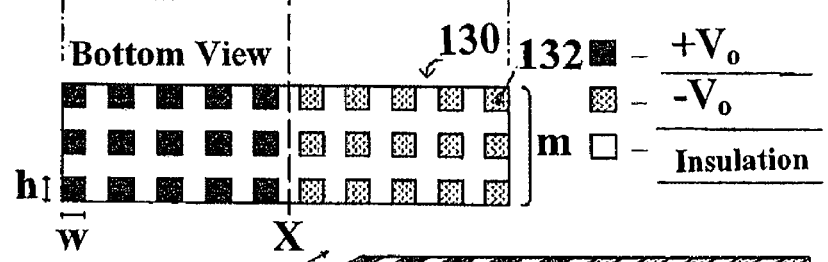
Figure 4C:
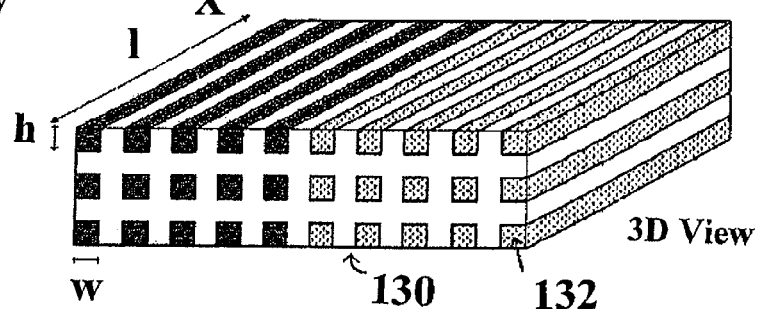

FIG. 4A, FIG. 4B, and FIG. 4C (collectively, FIG. 4) provide a side view, bottom view, and isometric view, respectively, of the sensor array 130. The following further describes one possible dimensional layout of the sensor array 130. The sensor array 130 provides for three-dimensional sample 120 characterization and imaging. The sensor array 130 contains a number of electrodes 132 that are arranged in a manner so as to maximize sensing performed by the sensor array 130, whether such sensing is for shallow sensing, mid sensing, or deep sensing. Arrangements of electrodes are described in further detail below.

FIG. 4 provides a basic electrode pattern containing a "2n× m" array of electrodes 132 located inside an insulating bulk. In accordance with the example illustrated by FIG. 4, "n"=5 and "m"=3, however, it should be noted that "n" and "m" can be any real positive integers.

For nano-scale imaging, the sensor array 130 is precision fabricated in layers. In the exemplary embodiment shown by FIG. 4, as best shown by FIG. 4B, the electrode array 130 may be fabricated in five (5) layers of Silicon dioxide ($SiO_2$) (a layer of periodically spaced electrodes, a layer of $SiO_2$ only, a layer of periodically spaced electrodes, a layer of $SiO_2$ only, and finally a layer of periodically spaced electrodes). It should be noted, however, that the sensor array 130 may instead be fabricated in a different material, as long as the material is a solid and insulating. In addition, each electrode 132 is preferably under one micron in size, and therefore is based on a nanometer scale, although as previously mentioned, electrode size is not required to be based on a nanometer scale.

As shown by FIG. 4B, the dimension 'w' represents the minimum width of the electrodes. The dimension 'h' represents the fabrication layer thickness, however, 'w' does not necessarily equal 'h'. The dimension 'l' represents the height of the electrodes 132, or the fabrication length. After fabrication, the face that is shown in FIG. 4B, namely, the bottom view, is polished so that the face is flat. Having the face flat provides for a more accurate maintenance of the sensor array 130 distance above the surface of the sample 120 and makes the sensor array 130 coplanar to planar substrates. It should be noted that there are many other useful faces, such as, for example, ones that are stepped, or curved if the top surface of the sample is stepped or curved.

As previously mentioned, the sensor array 130 may be used in an active mode or a passive mode. In the active mode, independent voltage or current sources are used to excite the individual electrodes 132 so as to allow for sample 120 characterization at different penetration depths. The process of exciting the individual electrodes 132 is described in additional detail below. Alternatively, in the passive mode, the electrodes 132 are not electrically driven, but instead used to sense electric or magnetic fields from the sample 120. Both the active mode and the passive mode are described in additional detail below. The following first describes the active mode.

Referring to FIG. 4, each electrode to the left of the denoted 'symmetry plane', shown as axis x, is excited by a sinusoidal, square, or any other special and temporal waveforms, relative to the electrodes to the right of the symmetry plane at frequency '$f_0$.' With this type of excitation, electrodes can be categorized by one of five types: drive electrodes, sense electrodes, guard electrodes, guard and drive electrodes, and guard and sense electrodes. The multi-element arrays are driven by a time-varying voltage that is applied to the electrodes in a desired pattern as a function of space, and resulting currents are acquired by the first module 210. It should be noted that arbitrary time domain signals may also be useful, for example, to measure relaxation phenomena.

Figure 5:
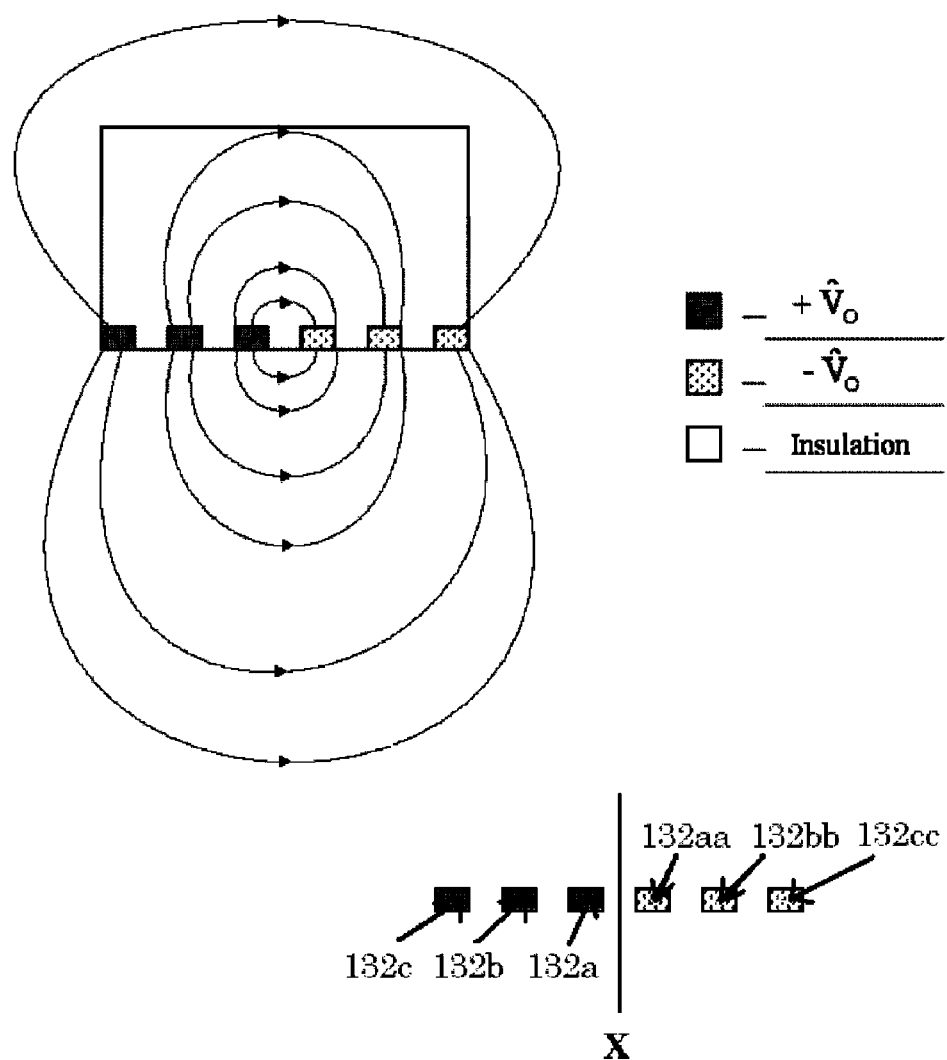
FIG. 5 is a schematic diagram illustrating pairs of electrodes and electroquasistatic fields that propagate from the electrode pairs.
Figure 6A:
FIG. 6A is a schematic diagram illustrating a line array of uniformly spaced electrodes.
Figure 6B:
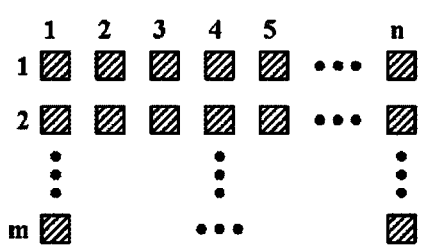
FIG. 6B is a schematic diagram illustrating a grid array of uniformly spaced electrodes.
Figure 6C:
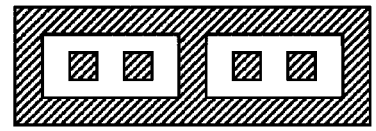
FIG. 6C is a schematic diagram illustrating a line array with guard rings.
Figure 6D:
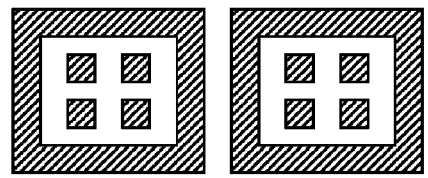
FIG. 6D is a schematic diagram illustrating a grid array with guard rings.
Figure 6E:
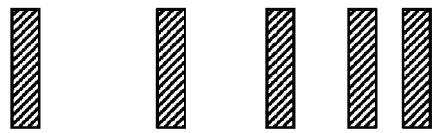
FIG. 6E is a schematic diagram illustrating non-uniformly spaced electrodes.
Figure 6F:
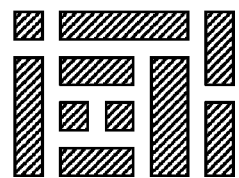
FIG. 6F is a schematic diagram illustrating a non-uniformly patterned array of electrodes.
Figure 7A:
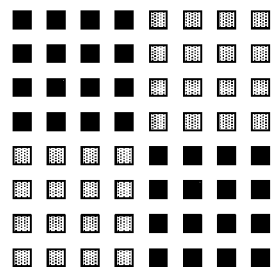
FIG. 7A is a schematic diagram illustrating a large-square checkerboard electrode pattern excitation.
Figure 7B:
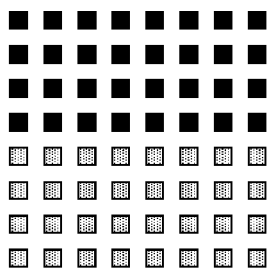
FIG. 7B is a schematic diagram illustrating a spatial step/square function.
Figure 7C:
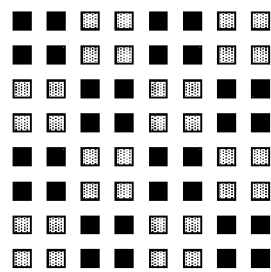
FIG. 7C is a schematic diagram illustrating a small-square checkerboard pattern excitation.
Figure 7D:
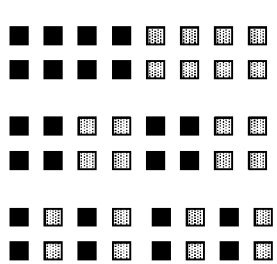
FIG. 7D is a schematic diagram illustrating varying spatial wavelengths.
Figure 7E:
FIG. 7E is a schematic diagram illustrating spatial step/square function with dedicated guard rings.
Figure 7F:
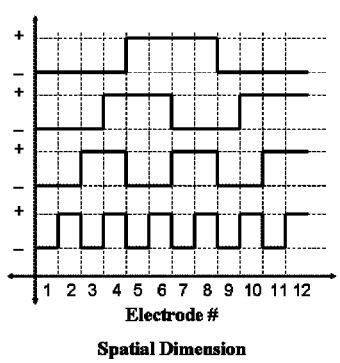
FIG. 7F is a schematic diagram illustrating varying spatial wavelengths along one spatial dimension by different excitation patterns, which can be extended to multiple dimensions.

In a differential drive scheme, each electrode to the left of the symmetry plane (x-axis) is paired with an electrode to the right of the symmetry plane. FIG. 5 better illustrates pairs of electrodes and electroquasistatic fields that propagate from the electrode pairs. Referring to FIG. 5, starting from closest to the symmetry plane (x-axis), a first electrode 132a is paired with a second electrode 132aa, a third electrode 132b is paired with a fourth electrode 132bb, and a fifth electrode 132c is paired to a sixth electrode 132cc. Each pair of electrodes is capable of penetrating the sample 120 at various depths based on their periodic spacing. The pair closest to the symmetry plane (x-axis) has a short depth of penetration, while the further the pair is from the symmetry plane (x-axis) the deeper the penetration of the quasistatic fields into the sample 120. An increasing number of pairs being further away from each other provide an increasing depth of penetration of a quasistatic field into the sample 120.

As is shown by the electrode pairs of FIG. 5, the electrode pairs provide electroquasistatic fields that extend in all directions. With the electroquasistatic fields extending in all directions it is desirable to concentrate the electroquasistatic fields in a direction so as to point the electroquasistatic fields toward a sample 120. Additionally, electrodes 132 within the sensor array 130 may also act as guards. Specifically, a second electrode, either concentric or adjacent to an electrode being used to provide an electromagnetic field, acts as a guard. The guard electrode is driven at the same potential and is used to minimize stray fields in the vicinity on the sample so that one only finds fringing fields off of the end of the field-providing electrode tip since fields have been shunted out of the tips of the electrodes through guarding. As a result, guards force the dominant electromagnetic fields to be directed toward the sample 120 that is being imaged.

Referring back to FIG. 4, in the excitation scheme, electrodes to the left of the symmetry plane (x-axis) are drives and/or guards, while electrodes to the right of the symmetry plane (x-axis) are sensors and/or guards. It should be noted that, in accordance with an alternative embodiment of the invention, the positions of the drives and sensors might be switched. In FIG. 4, the electrodes labeled as Y or YY are considered to be part of an active array 134, which is a portion of the sensor array 130. All electrodes on the perimeter of the active array 134, labeled in FIG. 4C with an X, should serve only as guard electrodes and can all be driven by the same source. The purpose of the guard electrodes is to guard the non-perimeter electrodes (non-perimeter electrodes are labeled in FIG. 4C with a Y or YY). The four pairs (or in general 'n−1' pairs) of non-perimeter electrodes can serve as both guard and drive/sense electrodes and should each be driven by separate sources, but at the same magnitude and phase as the guard electrodes. This allows for separate monitoring of impedance variations between each symmetry pair of drive/sense electrodes. This excitation scheme yields three fully guarded drive/sense electrode pairs and one pair of partially guarded drive/sense electrodes. It should be noted that this is only one specific drive scheme, each electrode is individually addressable, and there are many other drive patterns.

FIG. 6 is a schematic diagram illustrating different layouts for the electrodes in the sensor array 130. It should be noted that the present system and method may be used for many different unique layouts of electrodes. FIGS. 6A-6F (collectively, FIG. 6) provide examples of different sensor array layouts. Specifically, the present system may be provided with line arrays, grid arrays, guarded arrays, coaxial/concentric arrays, non-uniformly spaced electrode arrays, arrays designed for locating specific features, and other arrays.

Referring to images of FIG. 6: FIG. 6A provides a line array of uniformly spaced electrodes; FIG. 6B provides a grid array of uniformly spaced electrodes; FIG. 6C provides a line array with guard rings; FIG. 6D provides a grid array with guard rings; FIG. 6E provides non-uniformly spaced electrodes (in this case there is a spatial gradient in electrode density, but the layout could be random); and FIG. 6F provides a non-uniformly patterned array.

It should be noted that electrode excitations need not be limited to any specific patterns. If fact, with the many electrode layouts that may exist, there are also many creative spatial excitation patterns. Moreover, included in this set of excitation patterns are random excitation patterns.

Examples of sample excitations are provided by the schematic diagrams of FIG. 7. The figures of FIG. 7 provide the following: FIG. 7A provides a large-square checkerboard pattern excitation; FIG. 7B provides a spatial step/square function; FIG. 7C provides a small-square checkerboard pattern excitation; FIG. 7D provides varying spatial wavelengths; FIG. 7E provides spatial step/square function with dedicated guard rings; and FIG. 7F provides varying spatial wavelengths along one spatial dimension by different excitation patterns, which can be extended to multiple dimensions.

The present system measures the current/voltage relationship at every electrode, where the system can drive an electrode with a voltage and sense the resulting output current, or drive the sensor with a current and sense the resulting output voltage. It should be noted that each electrode may be individually addressable and detectable, as well as individually drivable. By individually addressing electrodes, the electrodes can be excited at the same magnitude and phase as their neighbor electrodes. This allows electrodes to serve the dual purpose of guarding and sensing.

In addition to a single-ended drive scheme, electrodes can be driven differentially in pairs. Also, not all electrodes have to be driven with a source. Some electrodes can be grounded, or left floating, and serve as dedicated sensing electrodes where the short-circuit currents or open-circuit voltages are measured.

In a passive implementation of the sensor array 130, as described below, none of the electrodes would be driven. Rather, the electrodes would be shorted, or left floating, and serve as dedicated sense electrodes. It is also important to note that excitation in the present system is not limited to a specific frequency, but rather a variable frequency drive can be used. This allows for investigation into the frequency dependent properties of the sample, which is useful for impedance spectral analysis.

Figure 8A:
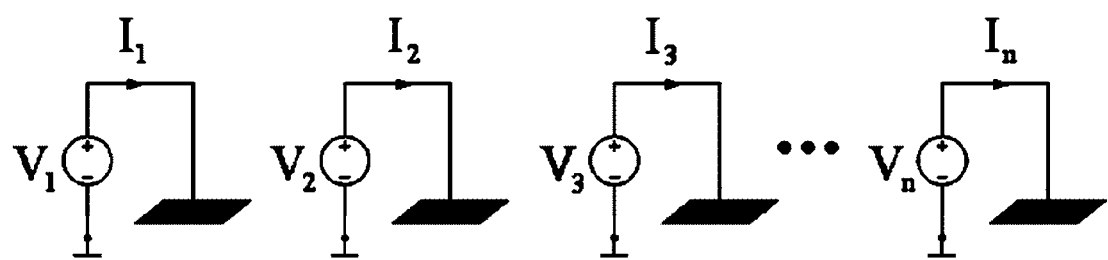
FIG. 8A is a schematic diagram providing an example of individually addressable electrodes where each electrode can be driven with a voltage source.
Figure 8B:
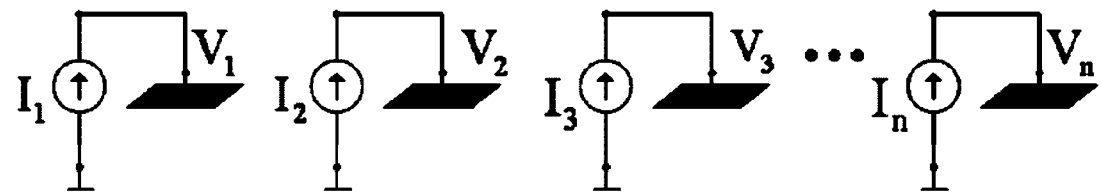
FIG. 8B is a schematic diagram providing an example of individually addressable electrodes where each electrode can be driven with a current source.

FIG. 8 is a schematic diagram providing examples of individually addressable electrodes. As shown by FIG. 8A, each electrode 132 can be driven with a voltage source, and its current is measured to determine self-impedance. Alternatively, as shown by FIG. 8B, each electrode can be driven with a current source and its voltage is measured to determine self-impedance. If there are n electrodes in the sensor array, then there are n branches in which current can flow. This creates a symmetrical impedance matrix where the diagonal terms are the self-impedance of each of the electrodes and the off-diagonal terms represent trans-impedances between electrodes. It should be noted that different methods of impedance detection may be used in accordance with the present invention and are intended to be incorporated by the present description. FIG. 3, which was described previously, provides one example of an impedance detection circuit that may be used in accordance with the present invention.

Figure 9:
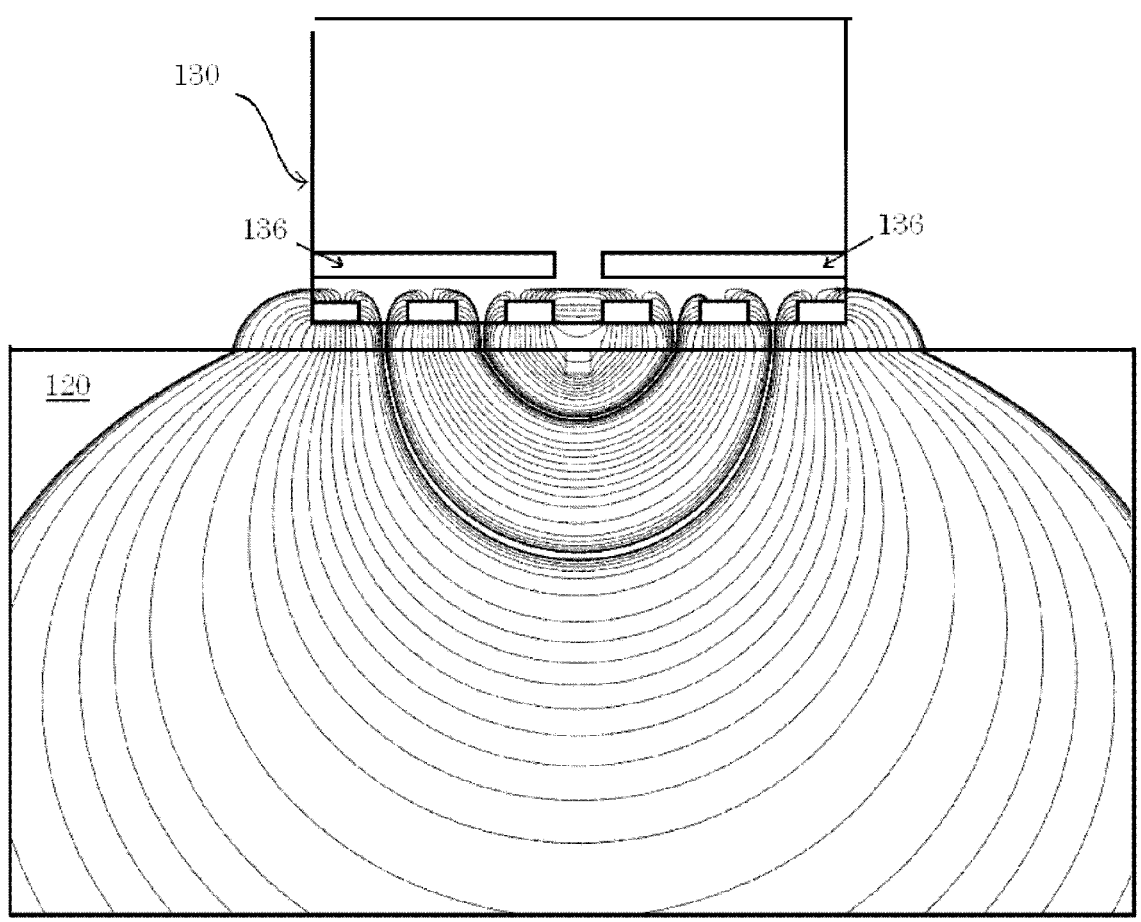
FIG. 9 is a schematic diagram providing a side view of drive and guard electrodes and electric field lines generated by a sensor array.

By fully guarding the drive/sense electrode pairs in the fashion mentioned above, a majority of the electric field generated by the drive electrodes is shunted through the sample 120. FIG. 9 is a schematic diagram providing a side view of the drive and guard electrodes and electric field lines generated by the sensor array 130. Shown in FIG. 9, but not in FIG. 4, are top-side guard electrodes 136. This top-side guarding is extremely helpful in blocking stray fields from having a strong influence on the impedance or admittance between drive/sense pairs.

By shunting the electric field through the sample 120, the total current density has maximum influence from the sample 120. Consequently, one observes maximum fluctuations in impedance/admittance between the drive/sense electrode pairs as they scan over different features of the sample 120. It should be noted, that in accordance with an alternative embodiment of the invention, one could implement an excitation scheme that does not utilize fully guarded electrodes, however, such a scheme would not be optimal for observing maximum impedance variations at the electrode terminals.

The schematic diagram provided by FIG. 9 provides visualization of the importance of fully guarding the electrode. Specifically, since most of the electric fields are shunted through the sample 120, the sense electrodes become sensitive to local changes in properties of the sample 120. The sensitivity of the sense electrodes makes the present system useful for detecting material interfaces, trenches, dust particles, and buried conductors, among other things. As stated previously, the depth of penetration of electric fields into the sample 120 is directly proportional to spacing between electrode pairs. It should be noted that in the present sensor array 130 one can simultaneously excite the sensor electrodes at different spatial wavelengths without any mechanical switching or motion. In addition, as each electrode pair penetrates the sample 120 to different depths, the electrode pairs also serve the purpose of guarding adjacent electrode pairs.

Figure 10A:
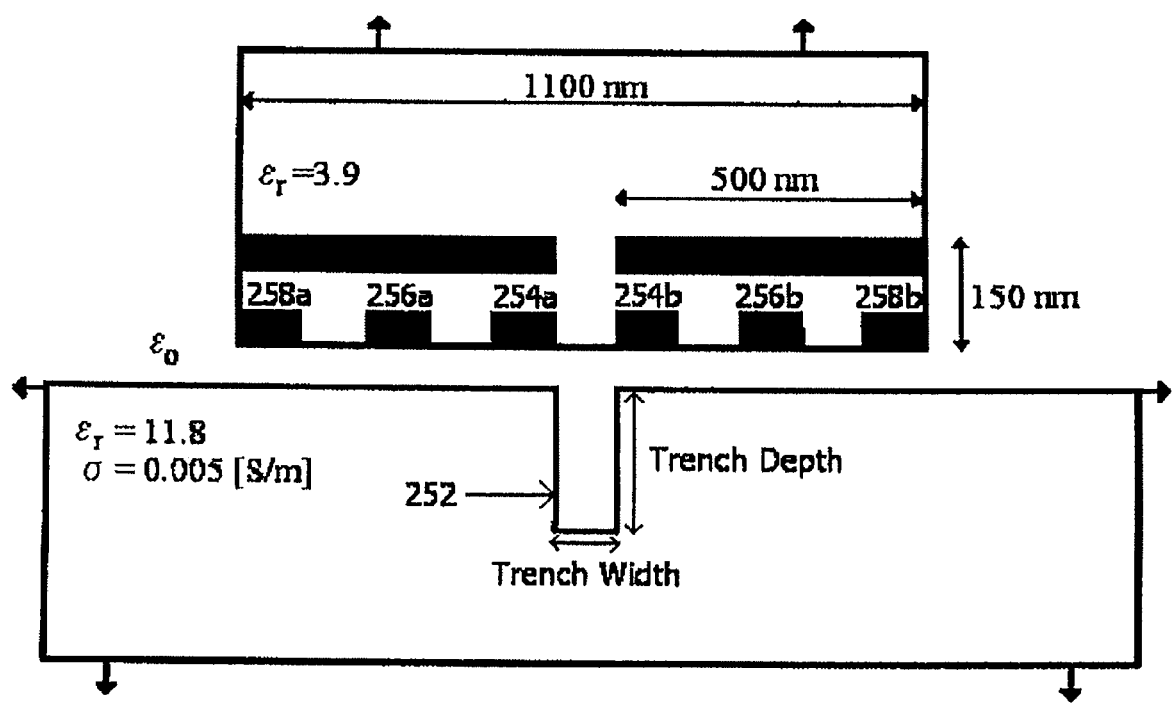
FIG. 10A is a schematic diagram demonstrating trench detection with the present system.

To demonstrate an example of use of the present system, FIGS. 10A, 10B, 11, 12A and 12B exemplify simulation results of detecting air-filled trenches in doped silicon in two dimensions (width and depth). FIG. 10A is a schematic diagram demonstrating trench 252 detection with the present system 100, in addition to exemplary dimensions used for a simulation. The width of the trench 252 is labeled "w" and the depth of the trench 252 is labeled "d". The number of electrode pairs used in this specific simulation was n=3, with a first electrode pair labeled as 254A and 254B, a second electrode pair labeled as 256A and 256B, and a third electrode pair labeled as 258A and 258B. This yields one fully guarded drive/sense electrode pair, namely the second electrode pair 256A, 256B.

Figure 10B:
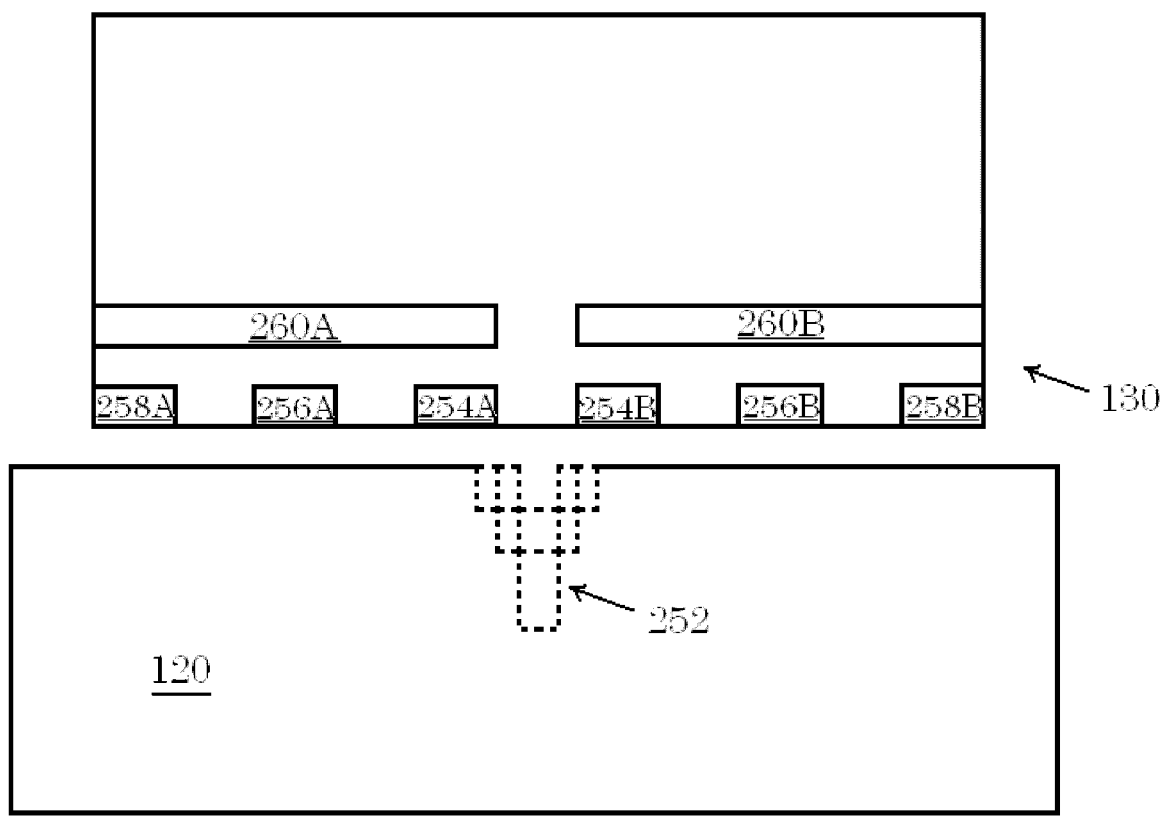
FIG. 10B is the schematic diagram of FIG. 10A, however with different labeling for better understanding.

FIG. 10B is the same schematic diagram of FIG. 10A, however with different labeling for better understanding of the system 100. The sensor array 130 contains a first guard electrode 260A and a second guard electrode 260B. In addition, the sensor array 130 contains a first sensor electrode 258A, a second sensor electrode 256A, a third sensor electrode 254A, a fourth sensor electrode 254B, a fifth sensor electrode 256B and a sixth sensor electrode 258B. Further, the trench 252 is located within the sample 120. For example, the sensor electrodes of FIG. 10B are capable of predicting the dimensions (depth and width) of a sub-micrometer scale trench in doped silicon based upon a measured transimpedance between two sensors in the sensor array when scanned laterally over the surface of the silicon.

Sensor electrodes 258A, 256A, 254A on the left half of the sensor array 130 are driven by a sinusoidally varying voltage source. This frequency is high enough such that it is on the order of the charge relaxation break frequency of the semiconducting silicon bulk, namely, the sample 120. Sensor electrodes 254B, 256B, 258B on the right half of the sensor array 130 are short-circuited to ground. The particular parameter of interest is the mutual transimpedance between the second sensor electrode 256A and the fifth sensor electrode 256B.

Figure 11:
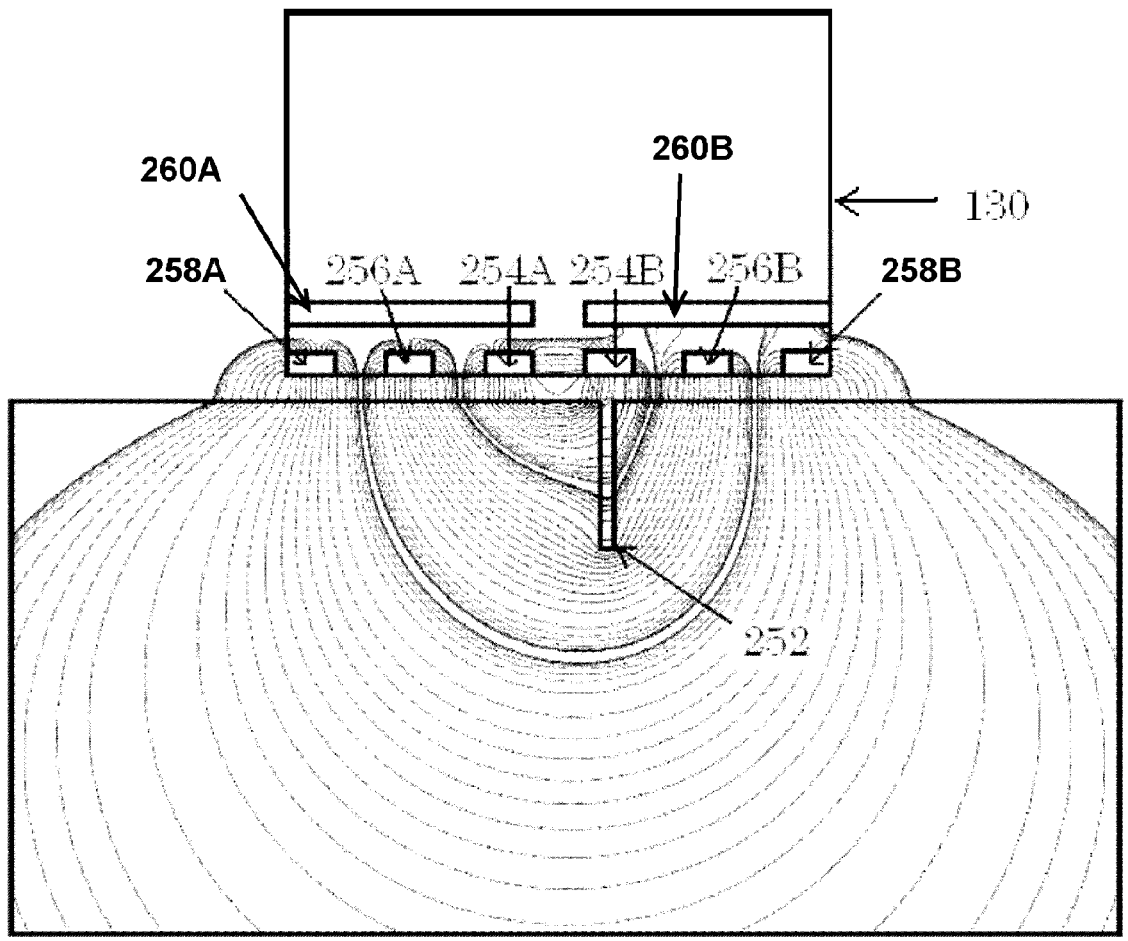
FIG. 11 is a schematic diagram illustrating electric field lines provided by the electrode pairs of FIG. 10A and FIG. 10B, being shunted through a doped silicon bulk.

FIG. 11 is a schematic diagram showing electric field lines provided by the electrode pairs of FIG. 10A and FIG. 10B, being shunted through a doped silicon bulk. By viewing FIG. 11, one can see how the electric fields react to the presence of the trench 252, which ultimately produces impedance variations at the electrode terminals. The electric field plot of FIG. 11 is for a high aspect ratio trench in the silicon bulk. Electric fields from the second sensor electrode 256A are shunted into the silicon bulk by guarding effects from the first sensor electrode 258A, the third sensor electrode 254A, and the first guard electrode 260A. These field lines can be seen bending and reacting to the presence of the air-filled trench 252. The presence of the air-filled trench 252 shows up as variations in both the magnitude and phase of the mutual transimpedance between the second sensor electrode 256A and the fifth sensor electrode 256B as the sensor array 130 scans past the trench 252. Other impedances may also be monitored.

Figure 12A:
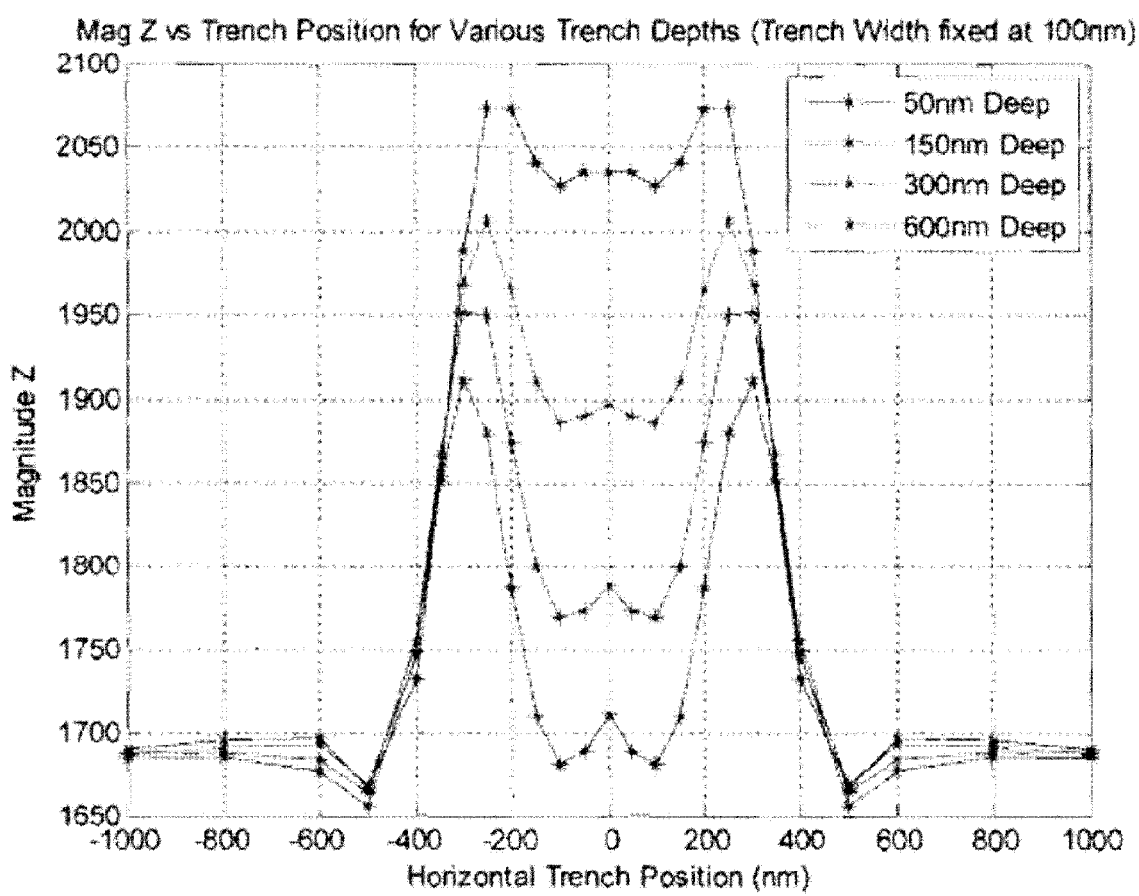
FIG. 12A and FIG. 12B are graphs illustrating changes in impedance between a fully guarded drive/sense electrode pair as they are scanned past trenches of various depths and widths.
Figure 12B:
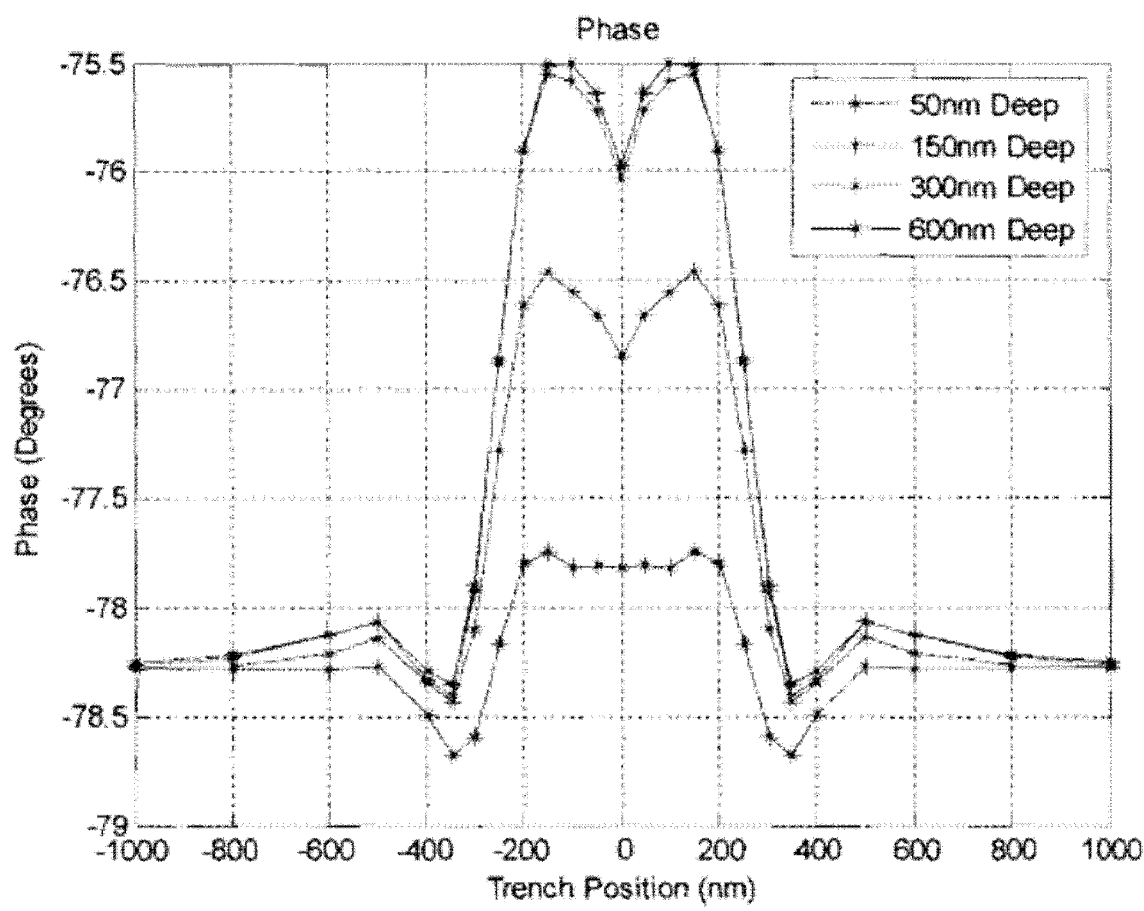

FIGS. 12A and 12B are graphs illustrating changes in impedance between the fully guarded drive/sense electrode pair 256A, 256B as they are scanned past trenches of various depths and widths. As shown by FIGS. 12A and 12B, the x-axis of the graph represents horizontal trench position in nanometers, while the y-axis of the graph represents magnitude. Graph lines demonstrate readings associated with trenches of 50 nm, 150 nm, 300 nm, and 600 nm in depth.

Figure 13:
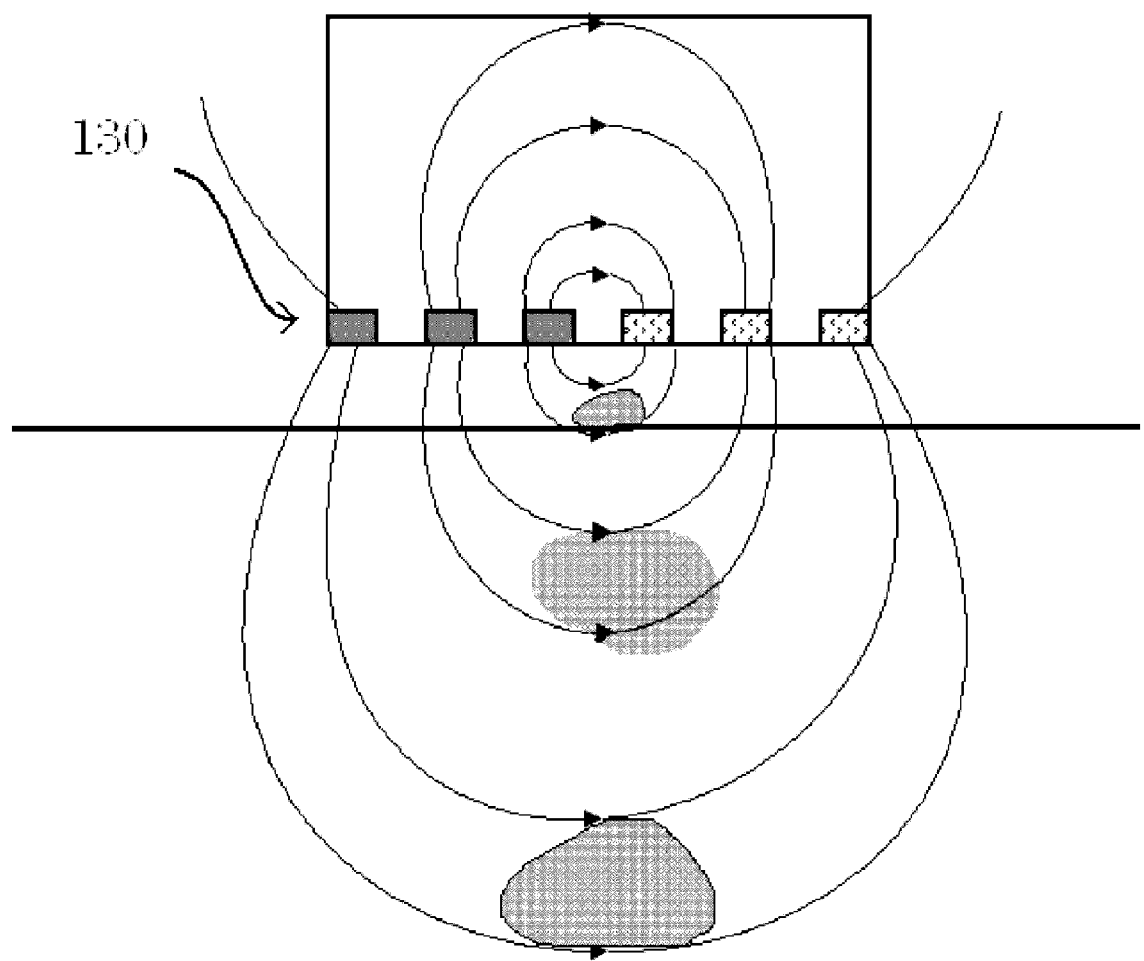
FIG. 13 is a schematic diagram illustrating sensor array detection of information regarding a sample at multiple depths.

It should be noted that the sensor array of the present invention is capable of simultaneously giving information about the sample at multiple depths with a spatial step/square excitation, as shown by FIG. 13. The impedance between the closest electrodes varies most strongly with shallow-depth variations in sample properties. A mid-distance pair reacts strongly to shallow objects, but also reacts to mid-depth variations that the close electrodes cannot. Furthermore, a widely separated pair is capable of detecting deeply buried objects that the shallow and mid-spaced electrodes cannot.

As previously mentioned, the sensor array 130 may also be used in a passive mode. In the passive mode electrodes can be used to listen for fields, rather than impose fields. The passive implementation of the sensor array 130 can be used for both the time and spatial monitoring of electrical signals along signal traces. Instead of driving the sensor array 130, a passive implementation leaves the electrodes 132 of the sensor array 130 unexcited. The sensor array 130 can then detect a signal by monitoring the spatial current or voltage profile that is induced along the sensor array 130 when it is in close proximity to a live signal.

The spatial profile provides information about signal strength, location, buried depth, and other features. Such an implementation is useful for monitoring signals in real-time and finding broken or flawed signal traces. As an example, in the passive implementation the electrodes act as passive listeners that allow for watching of currents to allow for the determination of performance of an active circuit. Specifically, the electrodes detect real-time electric fields from the live signals, while the circuit is in operation, thereby allowing for determination of which portions of the circuit are not working properly or are receiving delayed signals. The passive implementation is also convenient in that it does not require creative excitation and guarding schemes, but, as mentioned above, it can utilize the same exact electrodes as the active implementation.

Figure 14A:
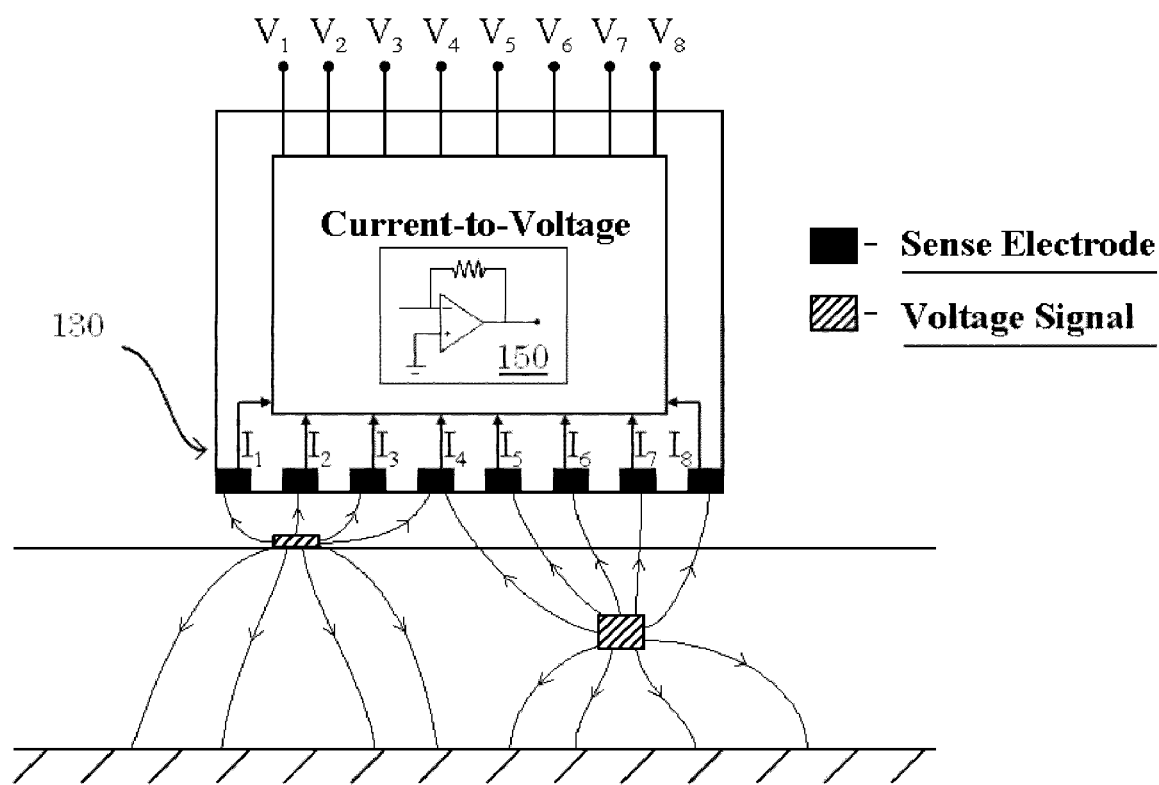
FIG. 14A is a schematic diagram illustrating a first example of a sensor array and drive/sense amplifiers when the sensor array is in a passive mode.
Figure 14B:
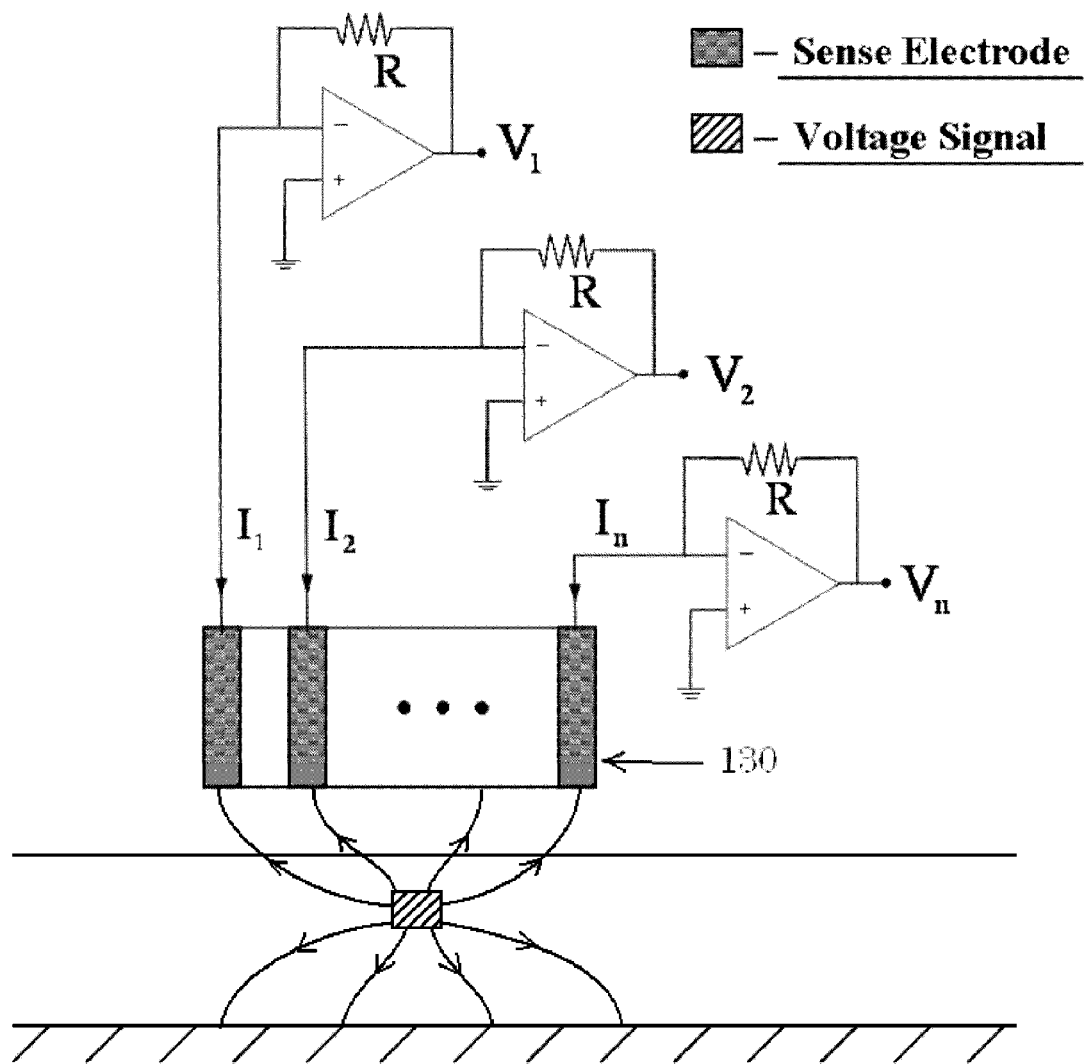
FIG. 14B is a schematic diagram illustrating a second example of a sensor array and drive/sense amplifiers when the sensor array is in a passive mode.

FIG. 14A is a schematic diagram illustrating a first example of the sensor array 130 and drive/sense amplifiers 150 when the sensor array 130 is in the passive mode. In addition, FIG. 14B is a schematic diagram illustrating a second example of the sensor array 130 which shows the internal circuit elements used in the drive/sense amplifiers when the sensor array 130 is in the passive mode. As previously mentioned, when brought into close proximity to a live signal, the sensor array will couple to the electrical signals on an integrated circuit or printed circuit. In both FIG. 14A and FIG. 14B, the sensor array 130 couples to the voltage signal line through the electric field of the voltage signal line. The currents that are induced on the sensor array can be amplified (for example, with current-to-voltage amplifiers). It is shown in FIG. 14A that the sensors are capable of passively detecting signals that run along the surface of the sample as well as signals that are buried in the substrate of the sample.

The current, or voltage, profile along the sensor array can provide information about the magnitude of the signal, timing, depth/distance of the signal, or simply the existence/nonexistence of the live signal. It should be noted that the previously mentioned properties of electrode spacing, pickup circuitry, impedance measurements, and other properties not only apply to the active mode implementation of the system, but also the passive mode implementation.

Referring back to FIGS. 12A and 12B, it is noted that the figures clearly indicate that scanning past trenches of various sizes and aspect ratios will produce different impedance/admittance variations between the drive/sense electrode pairs. This process may be referred to as the "forward problem." The "inverse problem" is then to reconstruct an image from the impedance/admittance data. Because the local impedance depends on the material properties of objects near the sensors, one can imagine the difficulty in reconstructing a unique and correct image in multi-layer, multi-material, inhomogeneous environments. In measuring samples, inverse problems involve the identification of defect parameters (e.g., length, width, depth, conductivity, etc.) from a measured signal. It is then possible to train an artificial neural network (ANN) based inversion algorithm to estimate an object based on those parameters. There is a wide variety of sources similar to the work done regarding the use of ANN and many other inversion algorithms for multi-channel signal inversion. As an example, tomographic imaging and inverse filtering would be equally applicable.

When imaging a sample, or surface of interest, to detect contamination particles, these particles will experience electromagnetic forces. In particular, if working in an electroquasistatic imaging mode, and if the particles have a dielectric constant larger than free space, the particles will experience an attractive force in the strong field region driven by the gradient of the electric field E.

This force may be used to attract the particles to the imaging electrodes, or to move the particles along the surface. In this fashion the imaging electrodes can be used to remove contaminating particles from a surface, thereby performing a cleaning function. For example, in the case of photomasks used to produce integrated circuits, contaminating particles produce errors in the circuits imaged from such photomasks.

The electromagnetic imager can be used to find such contaminating particles in an imaging mode. Then these particles can be targeted for removal via the electrostatic force from the array of electrodes. It may be desirable to increase the electrostatic force by using a larger voltage drive on the sensor array electrodes during such a cleaning process.

Such a cleaning process may also be facilitated by first charging the particles with electrons or ions to give the particles a net negative or positive charge. Then the particles will experience a force proportional to the net charge multiplied by the electric field. This may yield a larger force for particle removal and may help in attracting the contaminated particles to the electrode array.

When attempting to remove contamination particles, it may be helpful to vibrate the object surface rapidly, in order to dislodge the particles from the surface. Such vibration could be accomplished by shaking the clamp or chuck that holds the object to be imaged. Alternatively, transducers could be used to induce vibrations or waves in the object to be imaged. For example, traveling vibration waves in the object to be imaged will cause local displacements in vibration at the site of a contamination particle, causing it to be dislodged. Finally, such vibrations may be excited directly by forces from time-varying fields from the sensor array.

Figure 15:
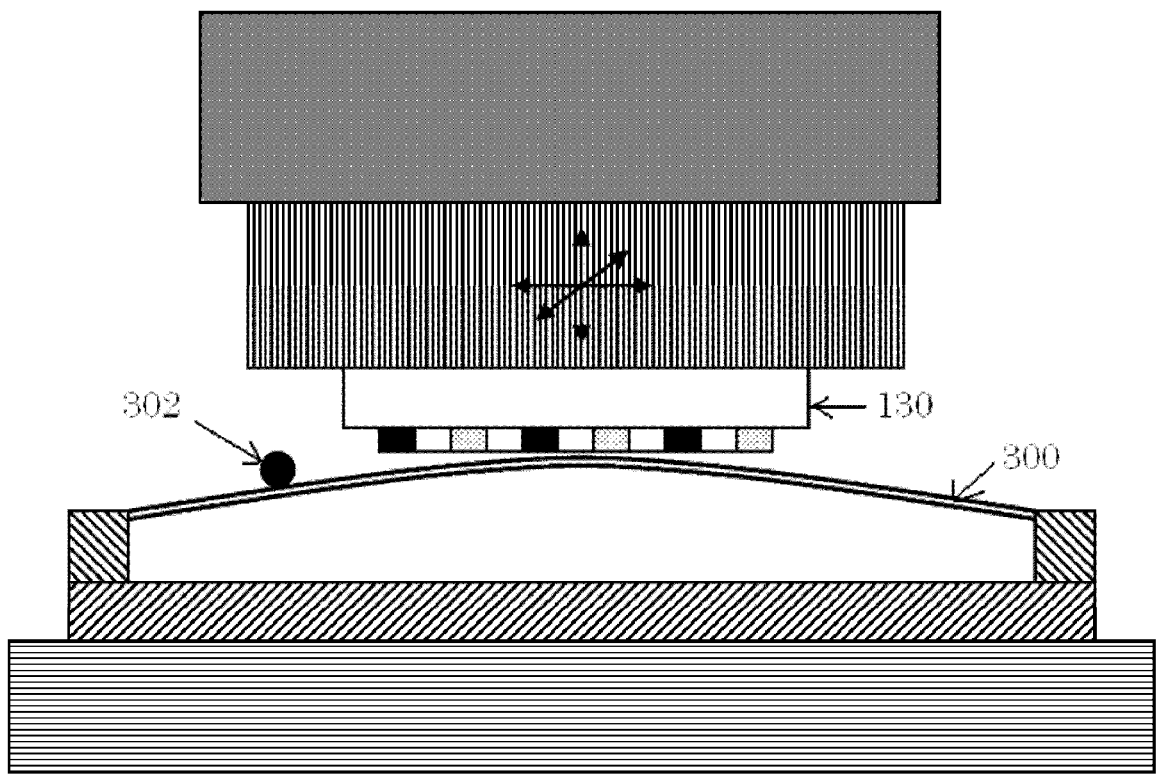
FIG. 15 is a schematic diagram demonstrating use of the present imaging system for particle removal.

FIG. 15 is a schematic diagram demonstrating use of the present imaging system for particle removal. FIG. 15 demonstrates pellicle attraction by the electric field of the sensor array where force on a dielectric is proportional to gradient of magnitude of E squared. The sensor array 130 is used to control the pellicle position. In addition, electric field forces are used to clean the pellicle by attraction, which may be helped by pre-charging particles 302 with ions of positive or negative polarity. In addition, particle transfer can be detected by change in capacitance, conductance, and/or impedance. The following further describes FIG. 15 in detail.

When imaging a flexible substrate, such as the pellicle 300 of an integrated circuit photomask, forces exerted by the sensor array electric field will cause the pellicle 300 to deflect as a membrane. These forces can be used to actively control the pellicle deflection in order to control the sensor array 130 working distance to the pellicle 300. Such forces might also be used to vibrate the pellicle 300 at a desired vibration frequency in order to facilitate particle 302 removal.

The electromagnetic imager design supports massive parallelism. That is, the electrode array can be made as large as desired in order to increase image throughput. For example, designs using thousands or millions of imaging electrodes or coils would allow parallel collection of thousands or millions of channels of imaging data, and thereby allow rapid imaging of a surface of interest.

Speed of detection of a defect or contamination particle could be enhanced also by first conducting a rapid survey with the probe elements driven with a lower spatial frequency excitation pattern, which thereby projects further from the array surface, with lower spatial resolution. Anomalies detected in this fast survey can then be imaged in more detail using a higher spatial frequency excitation pattern. This process would allow imaging time to be concentrated on the features or defects of interest.

In the case of detecting defects in an artifact such as a photomask or integrated circuit, the speed of detection may be augmented by working directly in the space of the raw imager data. For example, if the raw imager data is compared against the data from a known-good artifact, a deviation in this data can be detected directly. This can speed detection because the use of inverse algorithms is not required. That is, speed is enhanced by not undertaking the conversion from raw sensor data to image data.

The electromagnetic images can be used to scan biological materials, polymers, and plastics, and other materials with a dielectric constant and conductivity different from that of free space. It is also possible to use the electromagnetic images in operation in air, other gases such as helium or hydrogen, liquids such as water, or in vacuum or ultra-high vacuum. Imaging of bio-samples such as cells, viruses, cell components, and DNA is also possible. If these are imaged in an appropriate liquid, it is possible to image features of living cells.

Figure 16A:
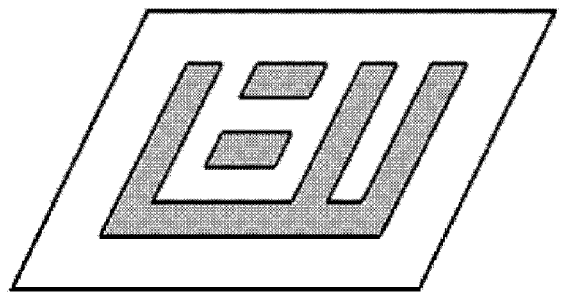
FIG. 16A is a schematic diagram illustrating an example of a clean photomask.
Figure 16B:
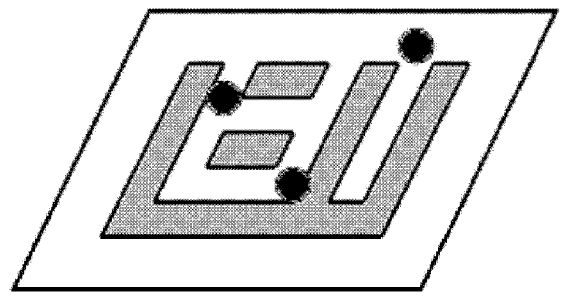
FIG. 16B is a schematic diagram illustrating an example of a photomask having contaminants thereon.

As previously mentioned the sensor array can be used to detect contaminant particles on the surface of the sample, such as, for example, contaminants on a photoreticles or pellicle. FIG. 16A is a schematic diagram providing an example of a clean photomask, while FIG. 16B is a schematic diagram providing an example of contaminants on a photomask.

Figure 17:
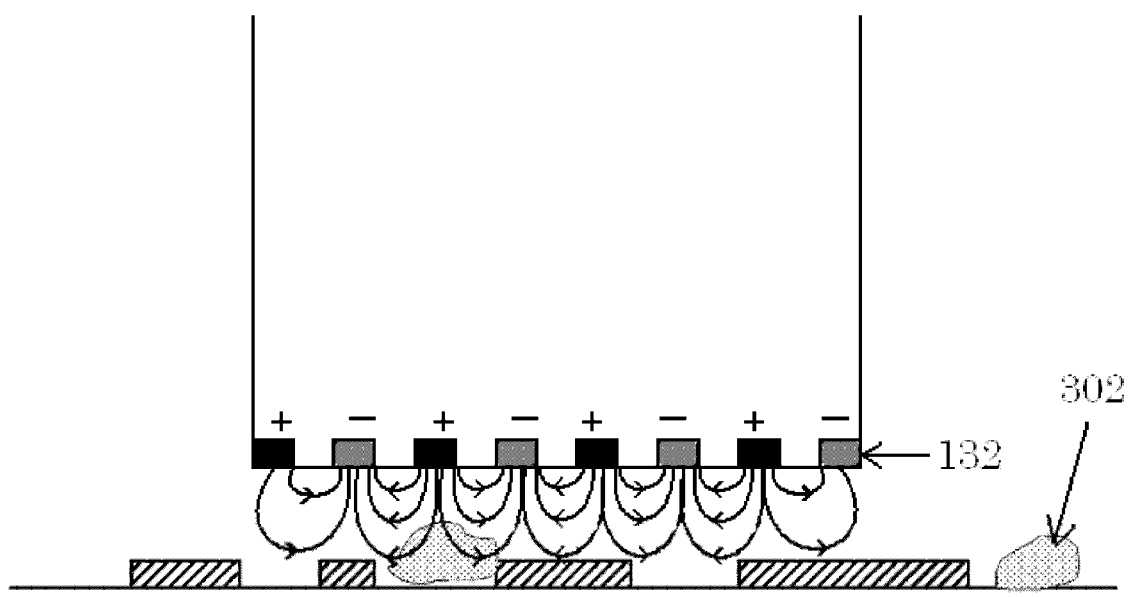
FIG. 17 is a schematic diagram illustrating exciting electrodes with a short spatial wavelength.
Figure 18:
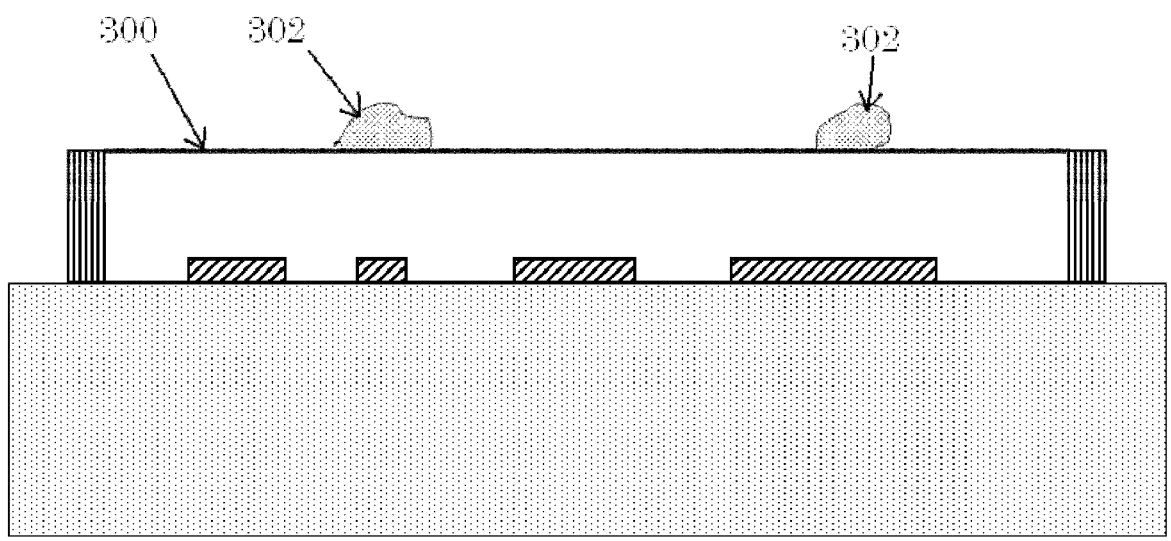
FIG. 18 is a further schematic diagram illustrating a contaminant on a pellicle.
Figure 19:
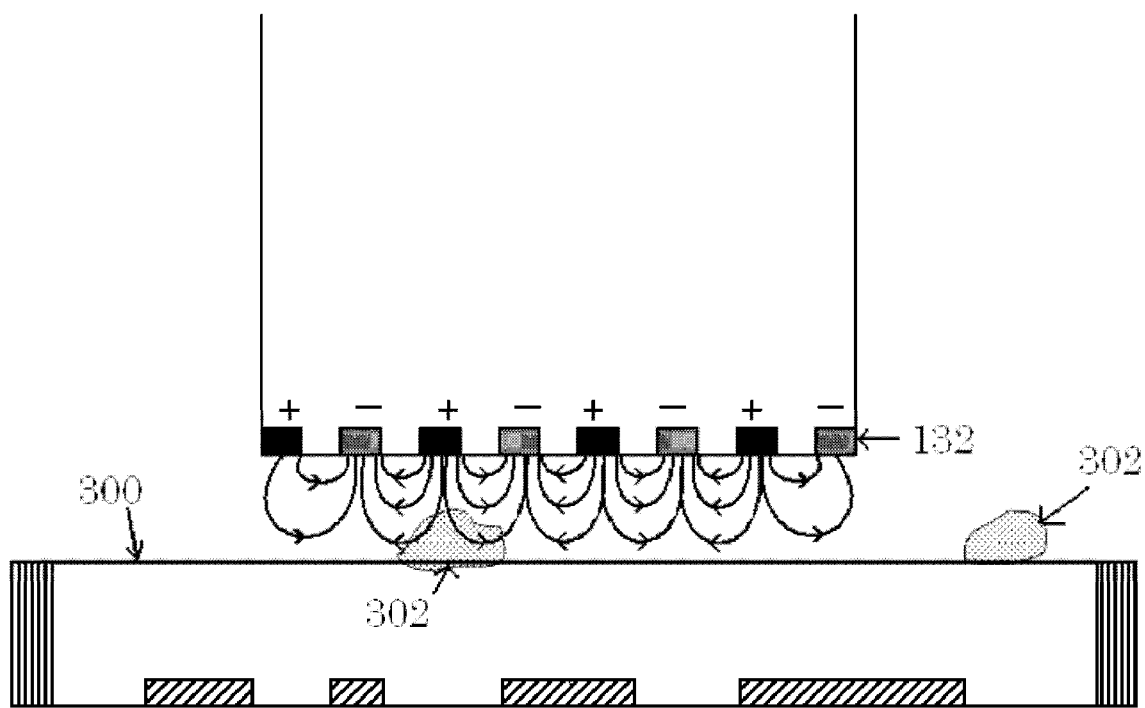
FIG. 19 is a schematic diagram illustrating particle detection.

By exciting the electrodes with a short spatial wavelength, as shown by FIG. 17, the range of evanescent fields of the electrodes 132 are limited. This forces the electrodes to react only to shallow/near surface variations. Ultimately, it is desirable to see fields reacting to particles on the surface of the mask/pellicle, but not deeply penetrating the bulk. This involves appropriately setting the scan height and electrode spacing. FIG. 18 is a further schematic diagram illustrating a contaminant 302 (particle) on a pellicle 300 and FIG. 19 demonstrates particle detection. It should be noted that another way to remove contaminant dielectric particles could be using a linearly traveling wave electric field.

Figure 20A:
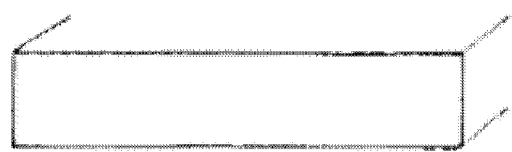
FIG. 20A-FIG. 20G are schematic diagrams illustrating a MEMS fabrication technique for a nanoscale electrode sensor array.
Figure 20B:
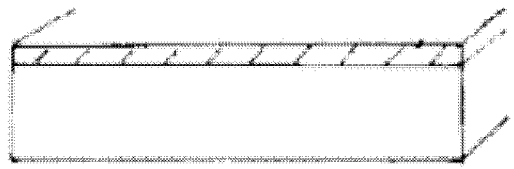
Figure 20C:
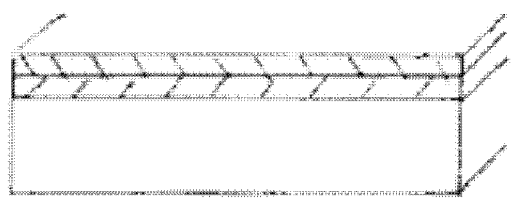
Figure 20D:
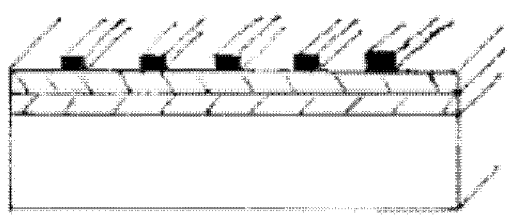
Figure 20E:
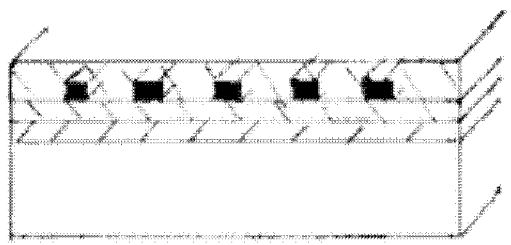
Figure 20F:
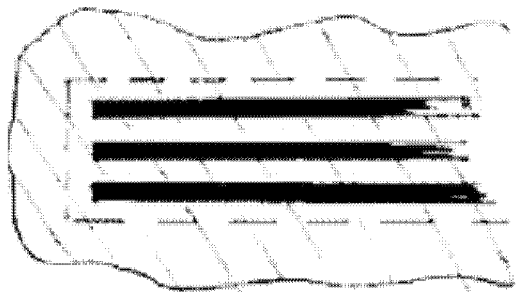
Figure 20G:
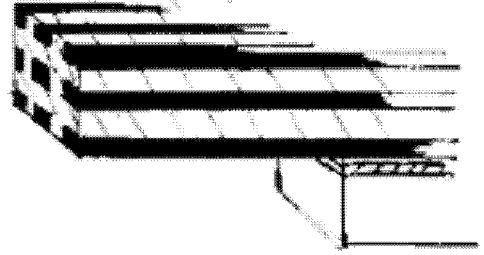

In accordance with one embodiment of the invention, the drive/sense amplifiers can be integrated circuitry on the silicon substrate, or surface mount electronics. FIGS. 20A-20G provide schematic diagrams illustrating a MEMS fabrication technique for a nanoscale electrode sensor array. As shown by FIG. 20A, the process begins with a Silicon substrate 310. An optional sacrificial nitride layer 312 is then deposited on the Silicon substrate 310 (FIG. 20B) after which an oxide layer 314 is deposited (FIG. 20C). A metal electrode pattern 316 is deposited on the oxide layer 314 (FIG. 20D). As shown by FIG. 20E, oxide is deposited for insulation between electrodes, after which additional metal electrode patterns may be provided to result in a desired number of electrodes. As shown by FIG. 20F, excess field oxide is etched away. An end face may then be created by lapping and polishing. Deep reactive-ion etching can be used to create an electrode array by removing the Silicon substrate. It should be noted that electronics can be microfabricated into the same substrate as the electrodes to maximize signal integrity and minimize noise.

Figure 21:
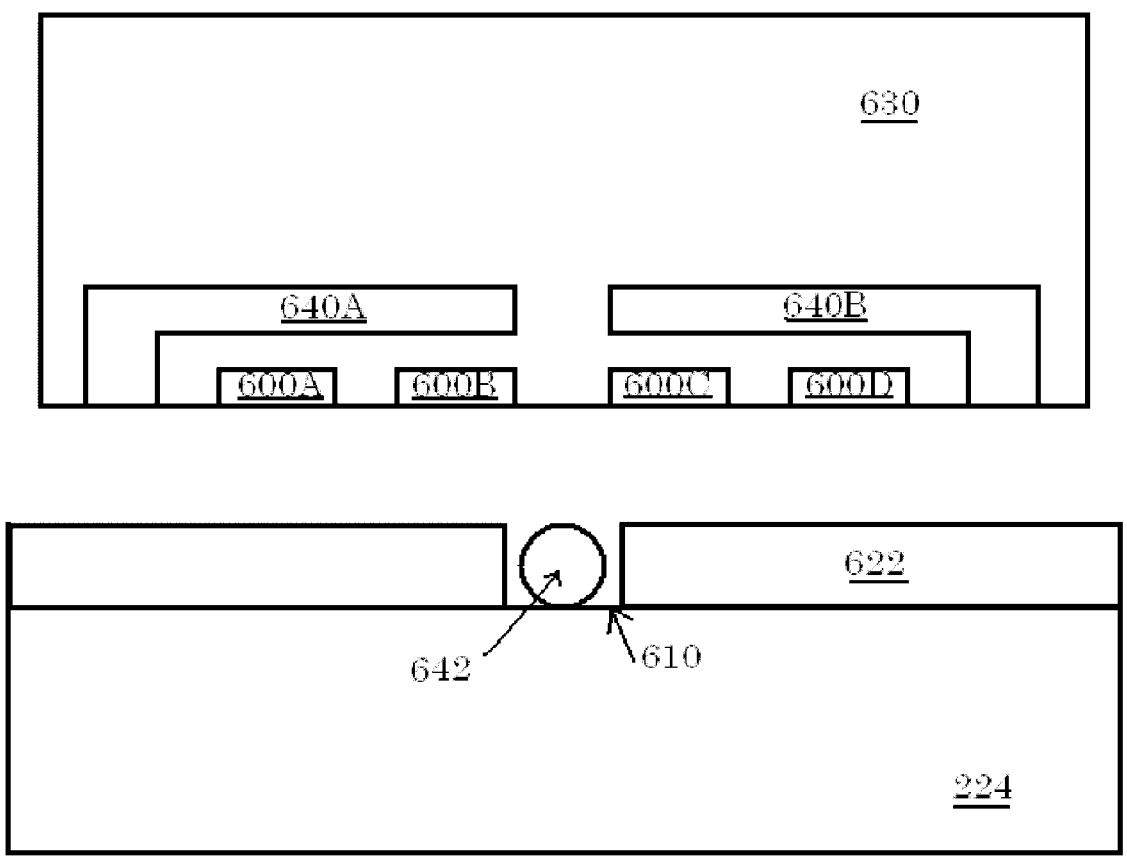
FIG. 21 is a schematic diagram illustrating an array of EQS sensor electrodes used to scan laterally past a gap in an absorber layer of a photomask.

FIG. 21 is a schematic diagram illustrating an array of EQS sensor electrodes 600A-600D used to scan laterally past a gap 610 in an absorber layer 622 of a photomask 624. There are four EQS sensor electrodes 600A-600D in a sensor head 630 and two dedicated guard electrodes 640A, 640B. Within the gap 610 is a contaminant particle 642. The sensor head 630 is scanned at a fixed height over the absorber layer 622. Contaminant particles of various different conductivity and permittivity might be located in the absorber layer gap 610 or on top of the absorber layer 622. Detecting a contaminant stuck in an absorber layer gap 610 represents a worst-case scenario since it is as far away from the sensor head 630 as possible.

Figure 22:
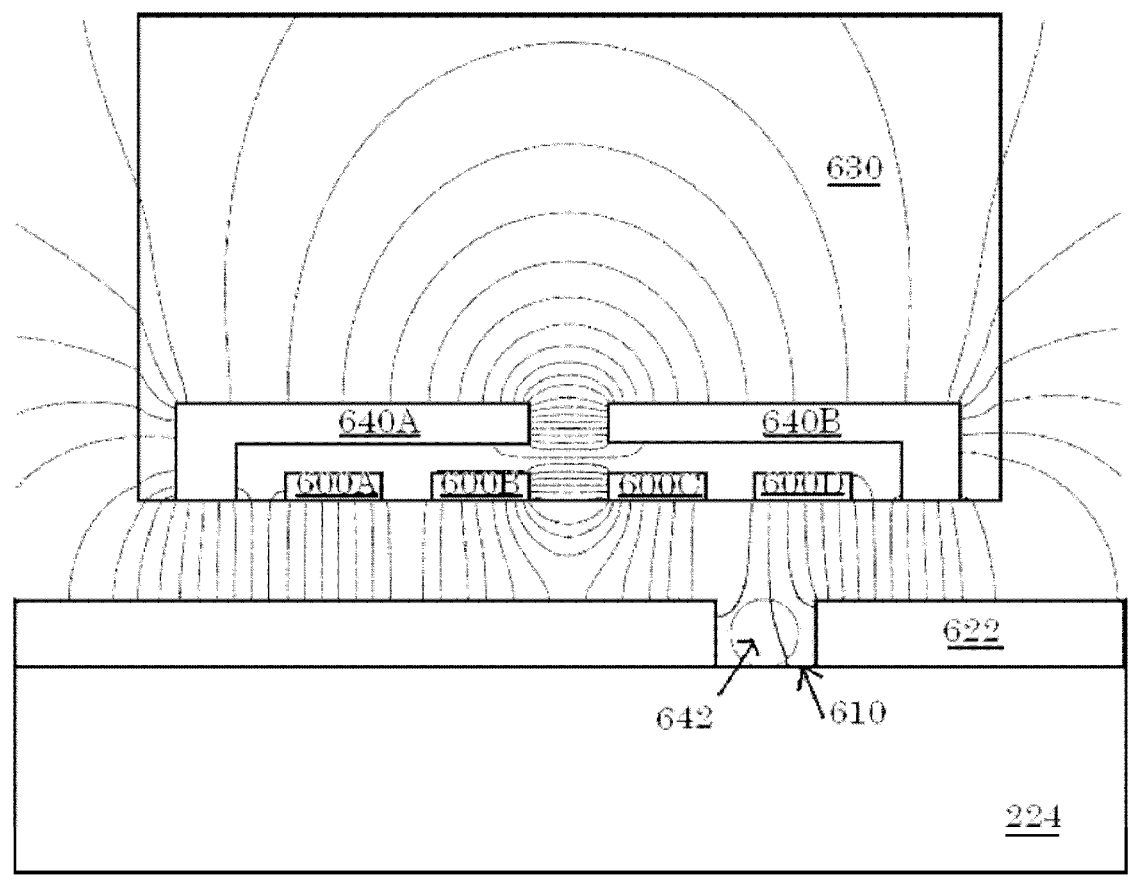
FIG. 22 is a schematic diagram illustrating electric field lines emanating from the EQS sensor electrodes of FIG. 21.
Figure 23A:
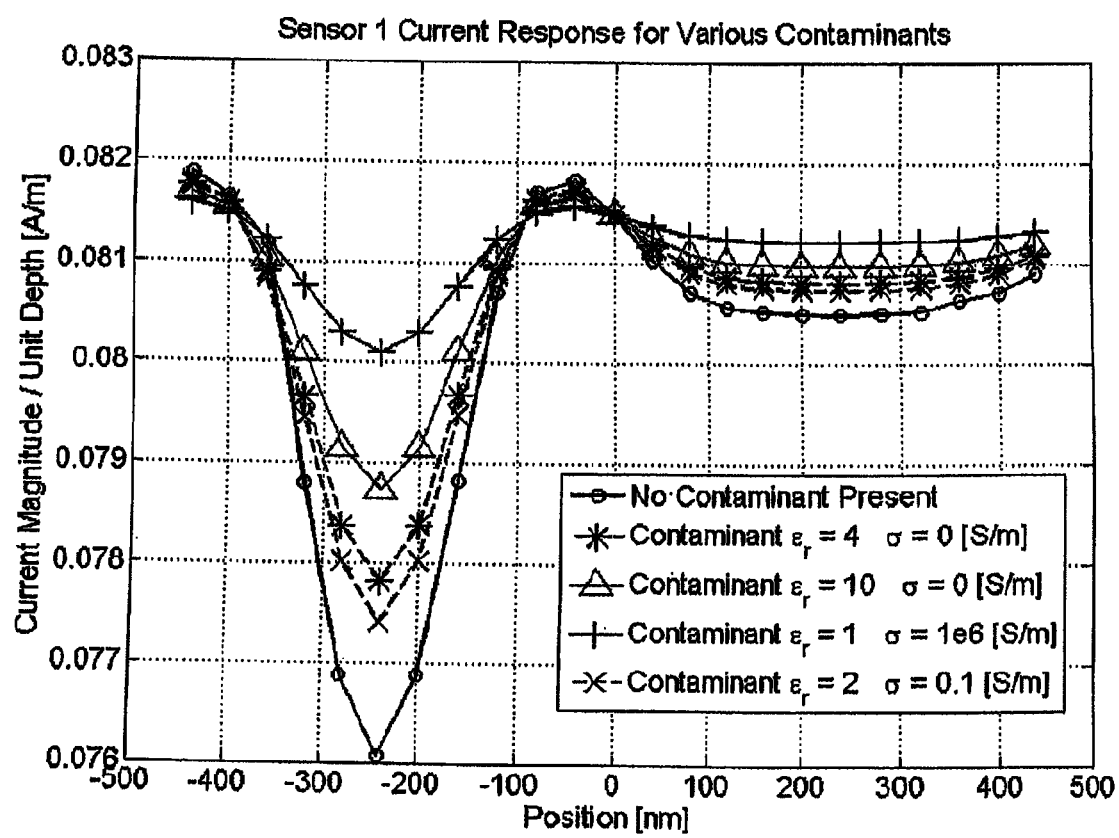
FIG. 23A-FIG. 23D are schematic diagrams plotting sensor electrode current magnitude responses for contaminants of various $\in_r$ and $\sigma$.
Figure 23B:
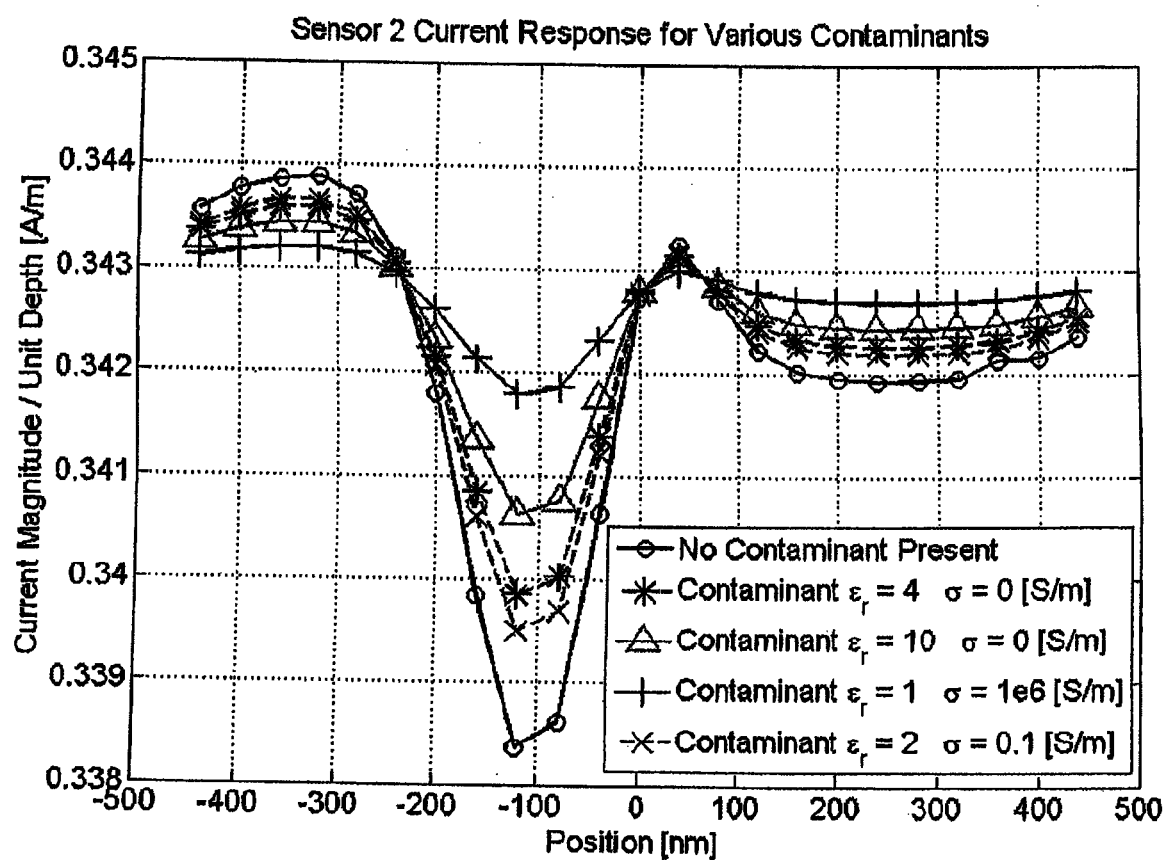
Figure 23C:
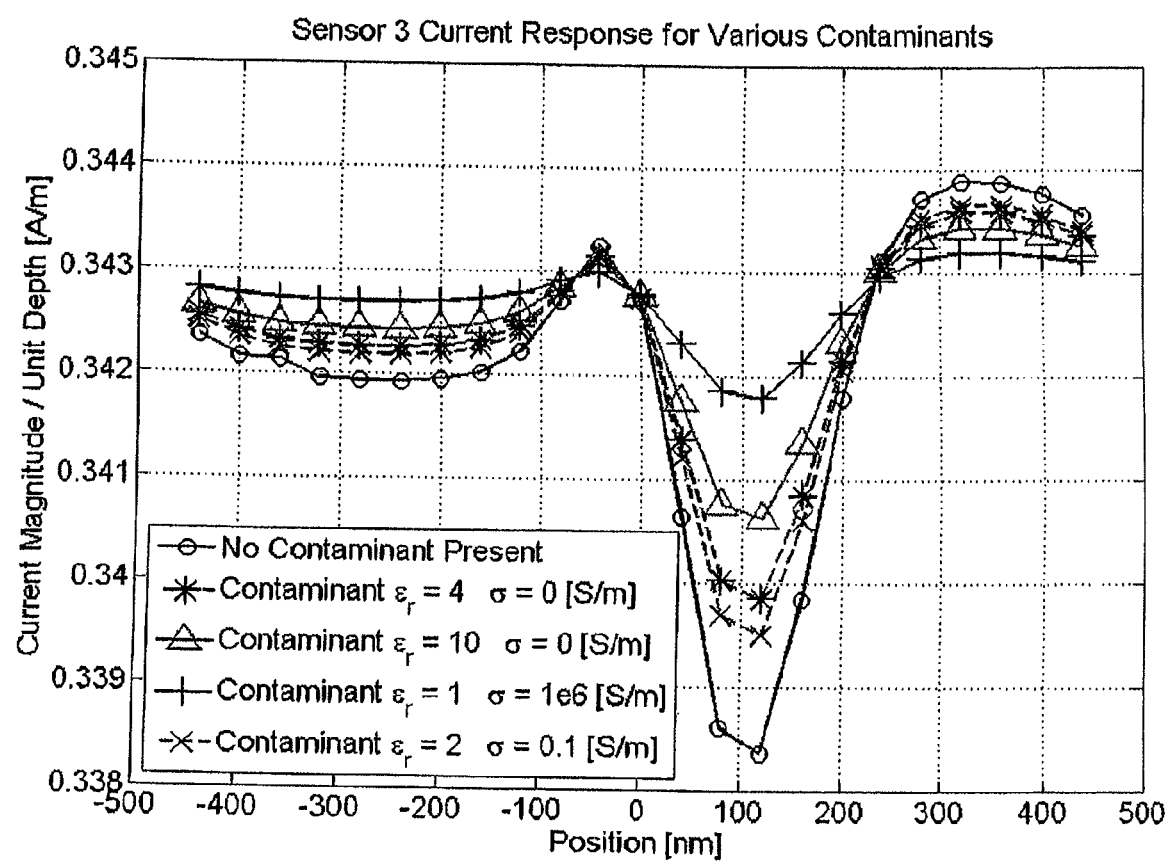
Figure 23D:
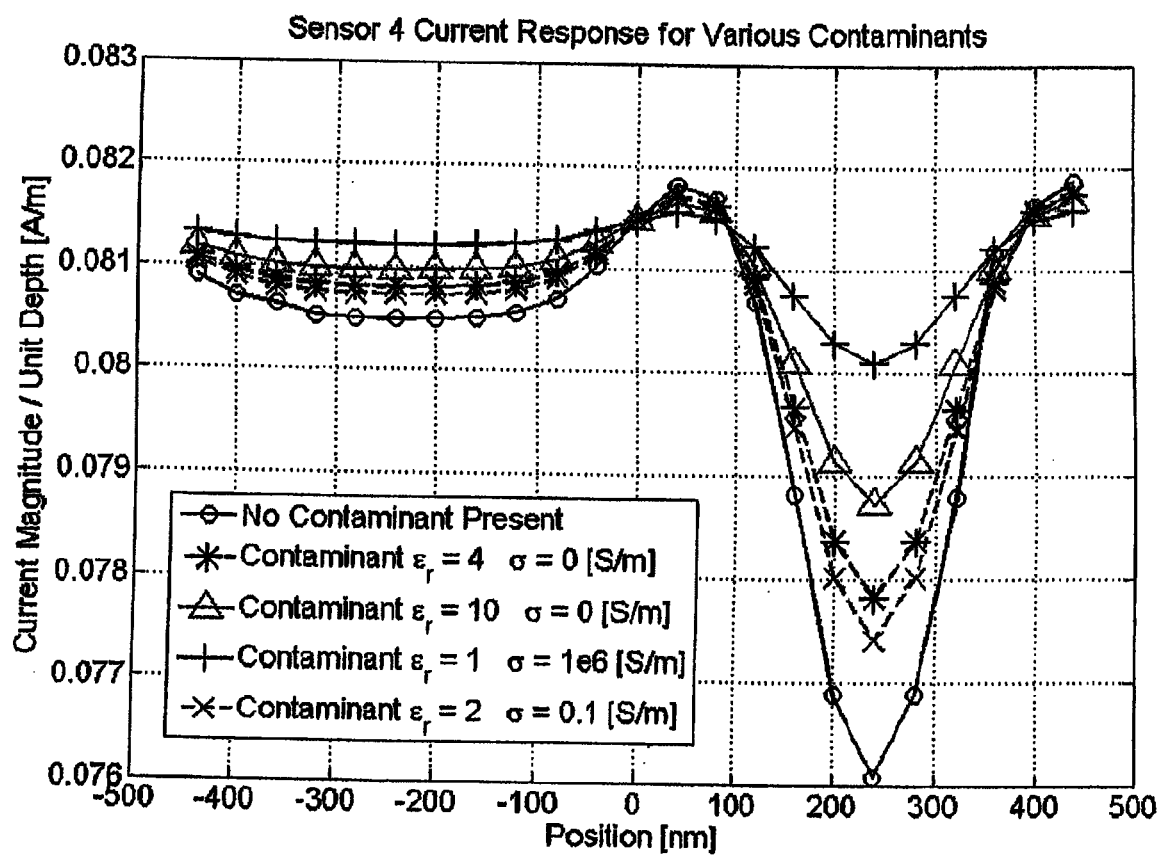

FIG. 22 is an electric field plot illustrating electric field lines emanating from the EQS sensor electrodes of FIG. 21. For exemplary purposes, a dielectric contaminant with $\in_r=4$ is positioned 200 nm to the right of the sensor head 630 center. The electric field lines from the first sensor electrode 600A are primarily vertical due to guarding effects caused by the second sensor electrode 600B and the first dedicated guard electrode 640A, which are driven at the same magnitude and phase as the first sensor electrode 600A. Since the absorber layer 622 is an excellent conductor, electric fields do not penetrate the surface of the absorber layer 622, but rather terminate on the surface. The high density of field lines located between the second sensor electrode 600B and the third sensor electrode 600C show that they are strongly coupled to each other in this region. Consequently, one can expect the second sensor electrode 600B and the third sensor electrode 600C to be poor at detecting the contaminant particle 642 when stuck in the absorber layer gap 610. Only a small portion of the fringing fields of the sensor electrodes 600B and 600C will couple to the contaminant particle 642. This manifests itself as only a weak change in current when these two sensors (600B and 600C) scan past the contaminant particle 642. Some of the fields from the fourth sensor electrode 600D are shown to pass through the dielectric contaminant particle 642, while others bend and terminate on the sidewalls of the absorber layer 622.

In accordance with one example of the invention, each sensor electrode can be driven by a sinusoidally varying voltage source. The third and fourth sensor electrodes 600C, 600D and the second guard electrode 640B shown in FIG. 22 are driven 180 degrees out of phase from the first and second sensor electrodes 600A, 600B and the first guard electrode 640A so as to create a spatial square wave alternating in time. The magnitude of each of the four sensor electrode currents as a function of sensor head position are monitored. It should be noted that sensor electrodes could also be driven by some other time-varying waveform that is not sinusoidal.

For exemplary purposes, each of the sensor electrode current magnitude responses are plotted in the graphs of FIGS. 23A-23D for contaminants of various $\in_r$ and $\sigma$. Due to symmetry of the sensor head geometry, the results for the first sensor electrode 600A and the second sensor electrode 600B are identical, but mirror images, of the results for the fourth sensor electrode 600D and the third sensor electrode 600C, respectively. The first sensor electrode 600A and the fourth sensor electrode 600D react more strongly to the absorber layer gap 610 than the second sensor electrode 600B and the third sensor electrode 600C. With no contaminant present, the first sensor electrode 600A sees approximately seven percent change in signal magnitude from the baseline value of 0.083 [A/m], while the second sensor electrode 600B yields only about a one and a half percent change in signal magnitude. In cases where the contaminant particle 642 is a strong dielectric ($\in_r=10$) or highly conducting ($\sigma=1e6$ [S/m]), the sensor electrodes can distinguish between a contaminated and clean gap with a difference in signal magnitude of four percent or more from what is expected for a clean gap. In the cases where the contaminant is a poor dielectric or is weakly conducting, the contaminant becomes increasingly more difficult for the sensor electrodes to distinguish between a contaminated and clean photomask.

Figure 24:
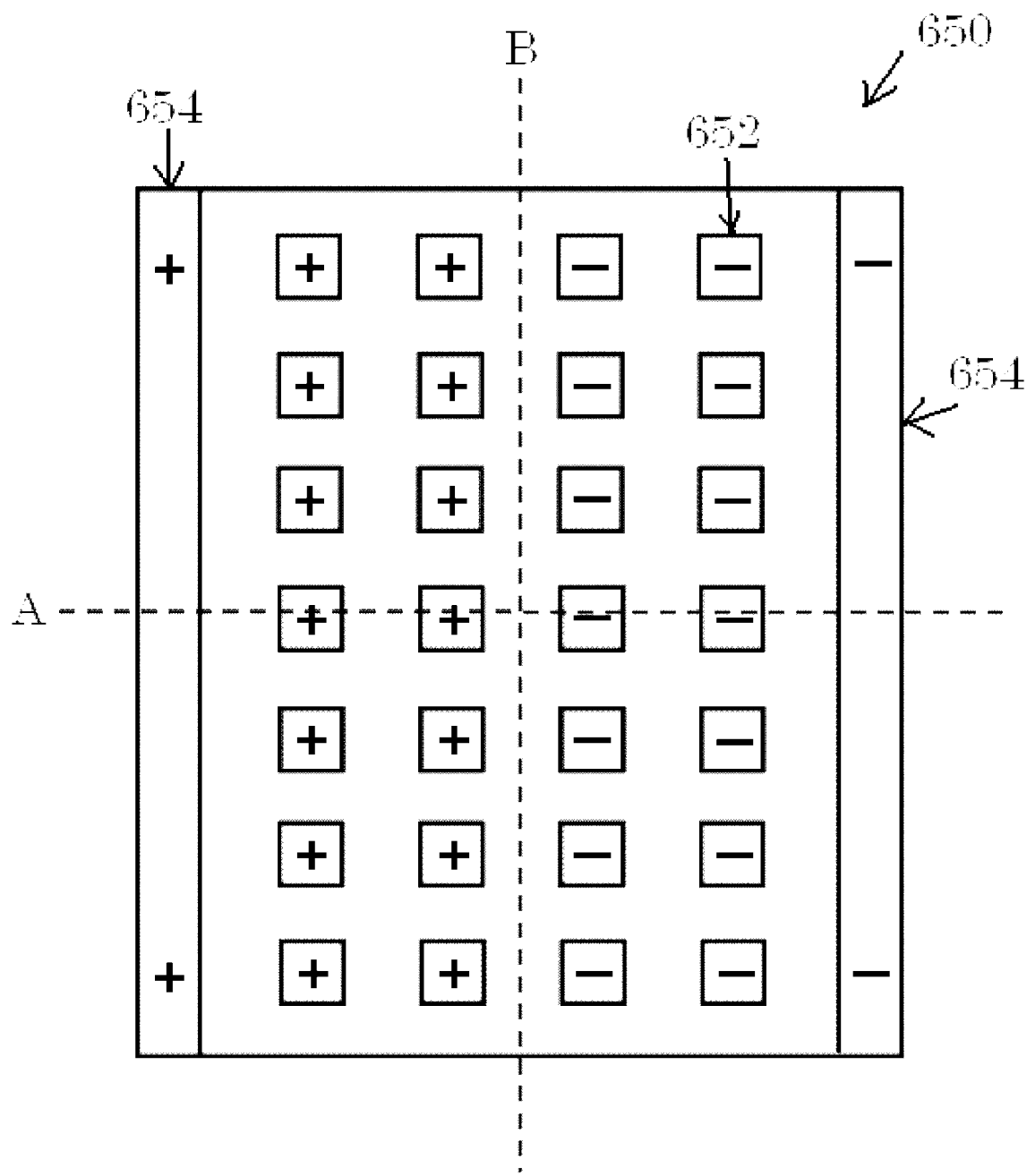
FIG. 24 is a schematic diagram illustrating an array-set of sensor electrodes.

The sensor electrodes shown in FIG. 21 and FIG. 22 can be part of an even larger array-set of sensor electrodes. FIG. 24 is a schematic diagram illustrating such an array-set of sensor electrodes 650. The array-set 650 contains a series of sensor electrodes 652 and two guard electrodes 654. The cross-section of the sensors and guards along axis A is equivalent to a bottom view of FIG. 21 and FIG. 22. Axis B provides a symmetry plane where everything to the left of the plane is driven at the same electric potential, while everything to the right of the plane is driven at the same electric potential.

Cross-section of the sensors and guards along axis B would represent those along line (A) of the figure. It should be noted that there can then be "n" many stacks of sensor electrodes in the sensor head. These sensor electrodes can form an "Electroquasistatic Brush" that "combs" over the surface of a photomask or other substrate for contaminants or defects with enormous parallelism.

Figure 25:
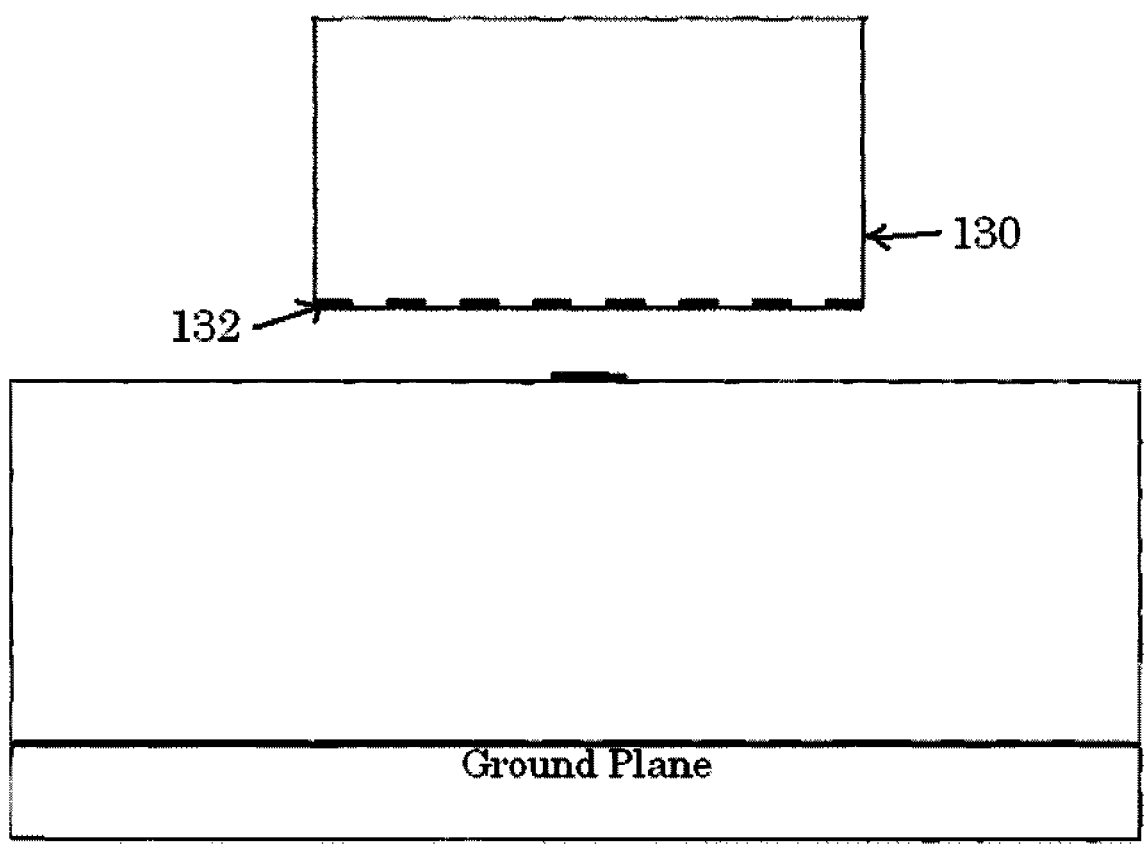
FIG. 25 is a schematic diagram illustrating simulated geometry in a passive implementation.
Figure 26:
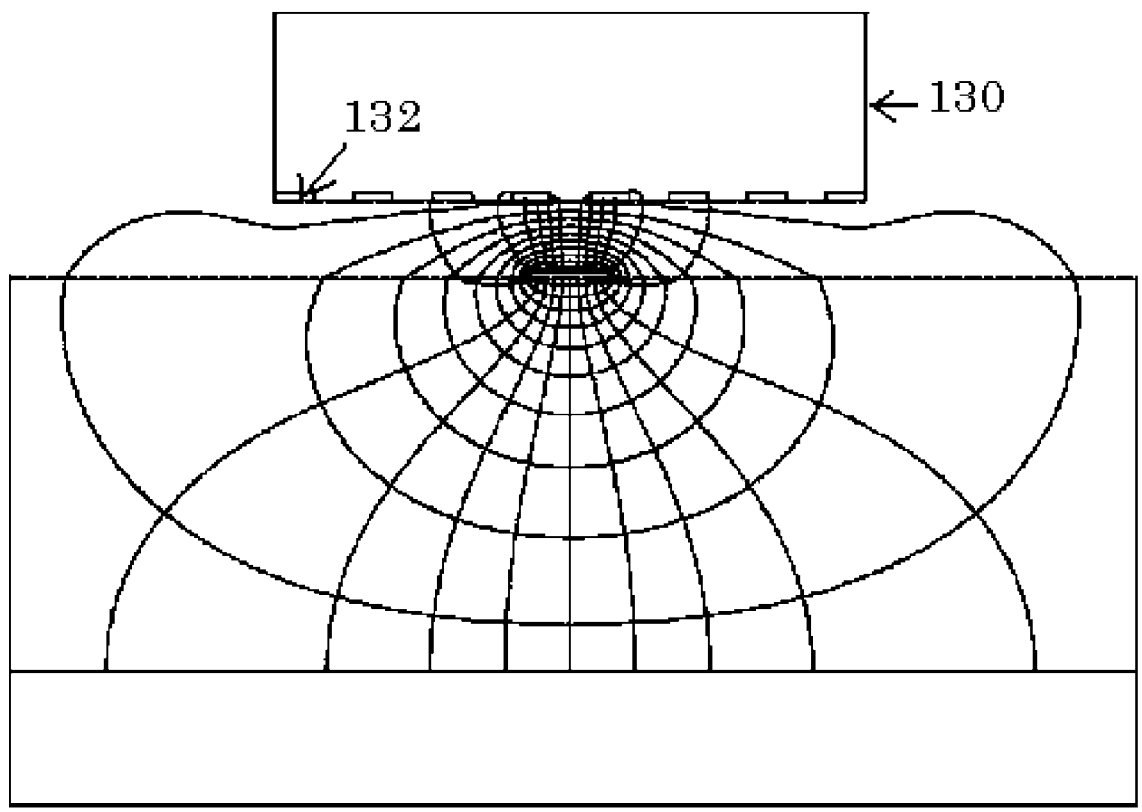
FIG. 26. is a schematic diagram illustrating sample electric field lines from a signal trace and illustrates the coupling between the trace and electrode array when they are in close proximity.
Figure 27:
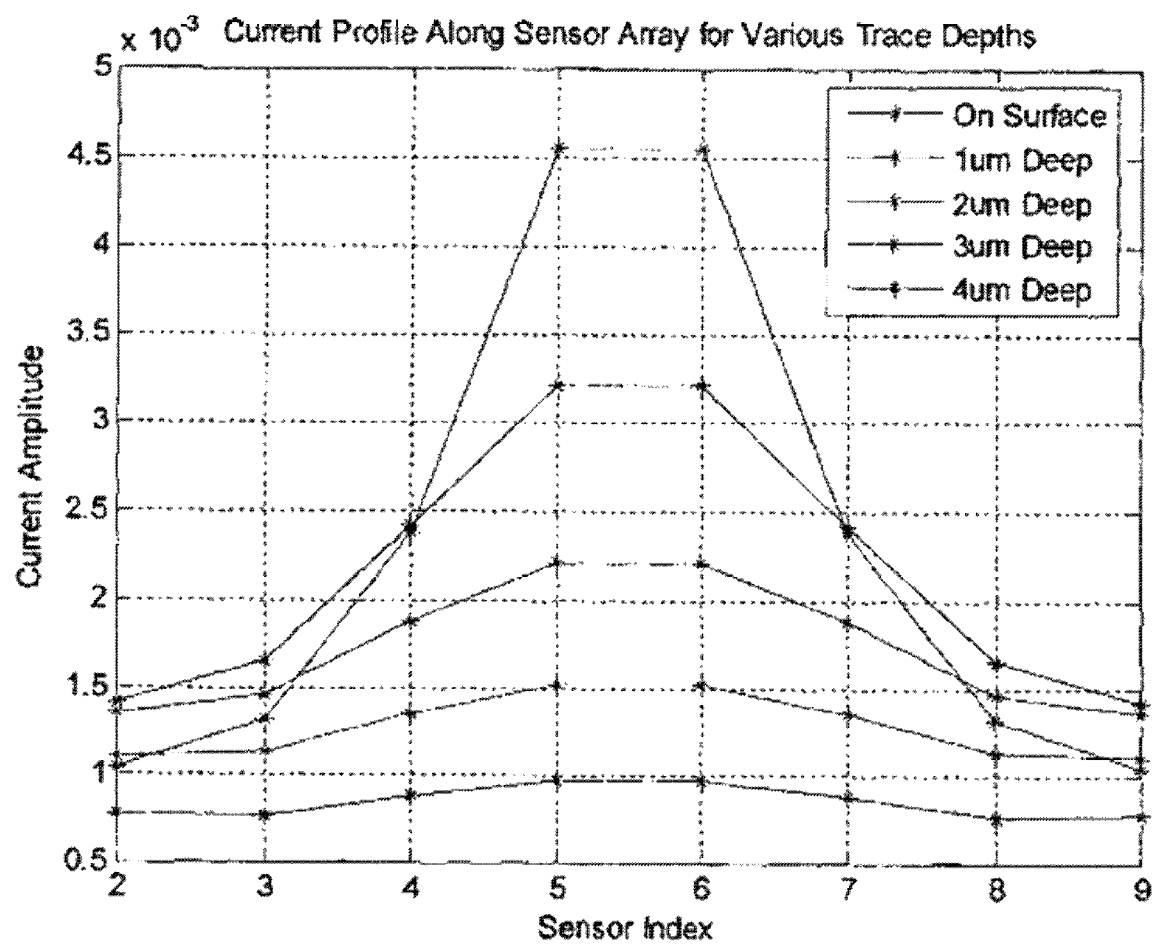
FIG. 27 is a schematic diagram illustrating the spatial current profile along the sensor array for various trace depths.

FIG. 25 illustrates simulated geometry in a passive implementation, for exemplary purposes. An array of eight electrodes is used and no top-side guard electrodes are present. While one could use an array that has top-side guard electrodes present, it is not necessary since this is a passive implementation. The signal line is excited by an AC signal of 1V at 100 MHz. The line is buried at five different depths: 0 μm (shown), 1 μm, 2 μm, 3 μm, and 4 μm. The electrodes 132 in the array 130 are grounded and their short circuit currents are monitored. FIG. 26 shows sample electric field lines from the signal trace and illustrates the coupling between the trace and the electrode array 130 when they are in close proximity. FIG. 27 shows the spatial current profile along the sensor array for various trace depths. One can see that as the trace gets further from the sensor array, the profile begins to both smear out and decrease in amplitude.

Figure 28:
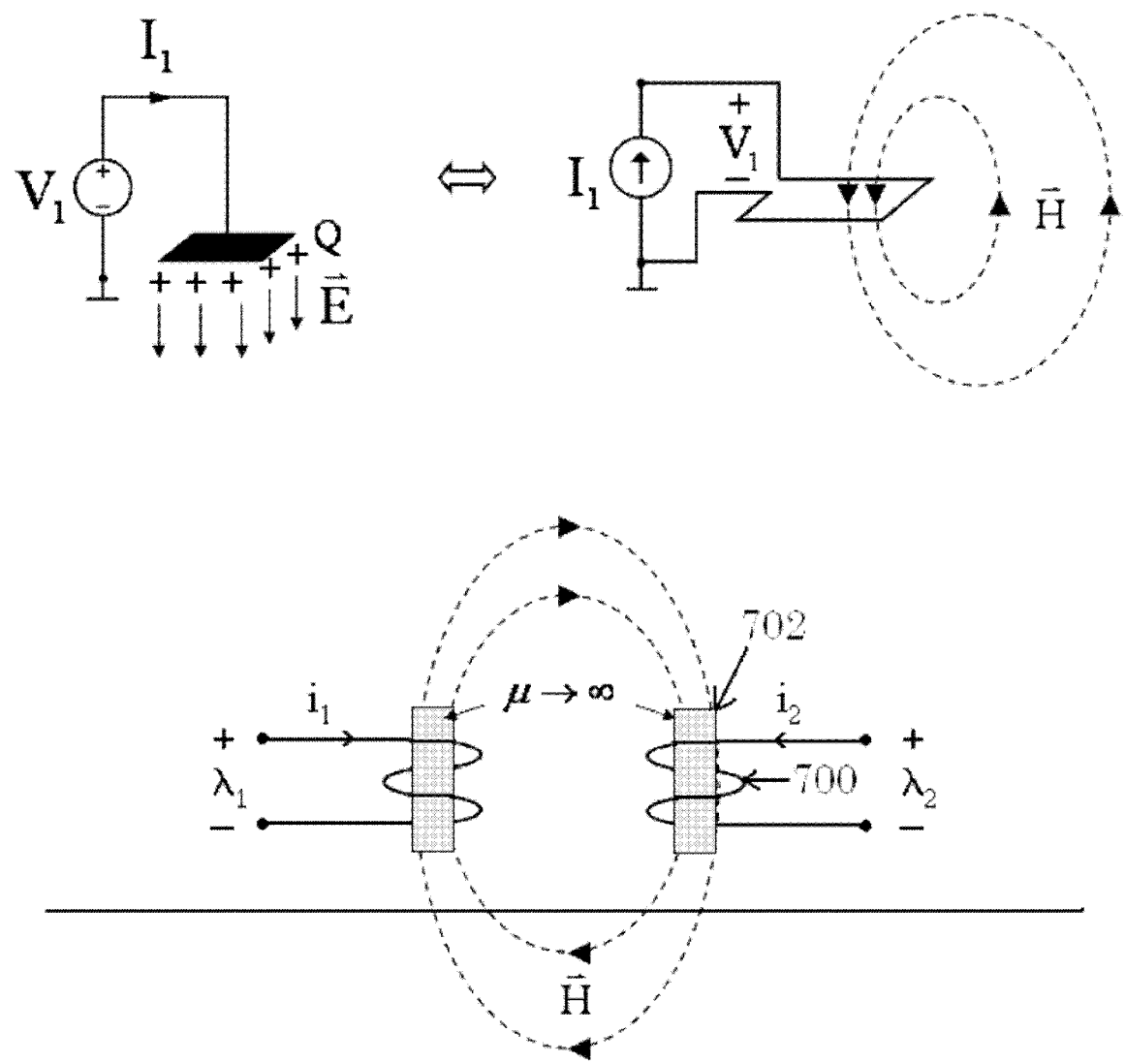
FIG. 28 is a schematic diagram illustrating a magnetic field created by current about a loop.

As previously mentioned, the present system and method may also contain a magnetically driven electromagnetic sensor array. The magnetoquasistatic (MQS) analog to an individual electroquasistatic (EQS) sensor is a small and individually addressable conducting loop. Current about the loop creates a magnetic field much like charge on the electrode creates an electric field, as shown by FIG. 28. As shown by FIG. 28, the loop 700 can have multiple turns, and can have a high-permeability core 702. In addition, the loop 700 can have multiple (primary and secondary) windings. Further, small permanent magnets can be implemented to generate the magnetic fields (not shown).

Figure 29:
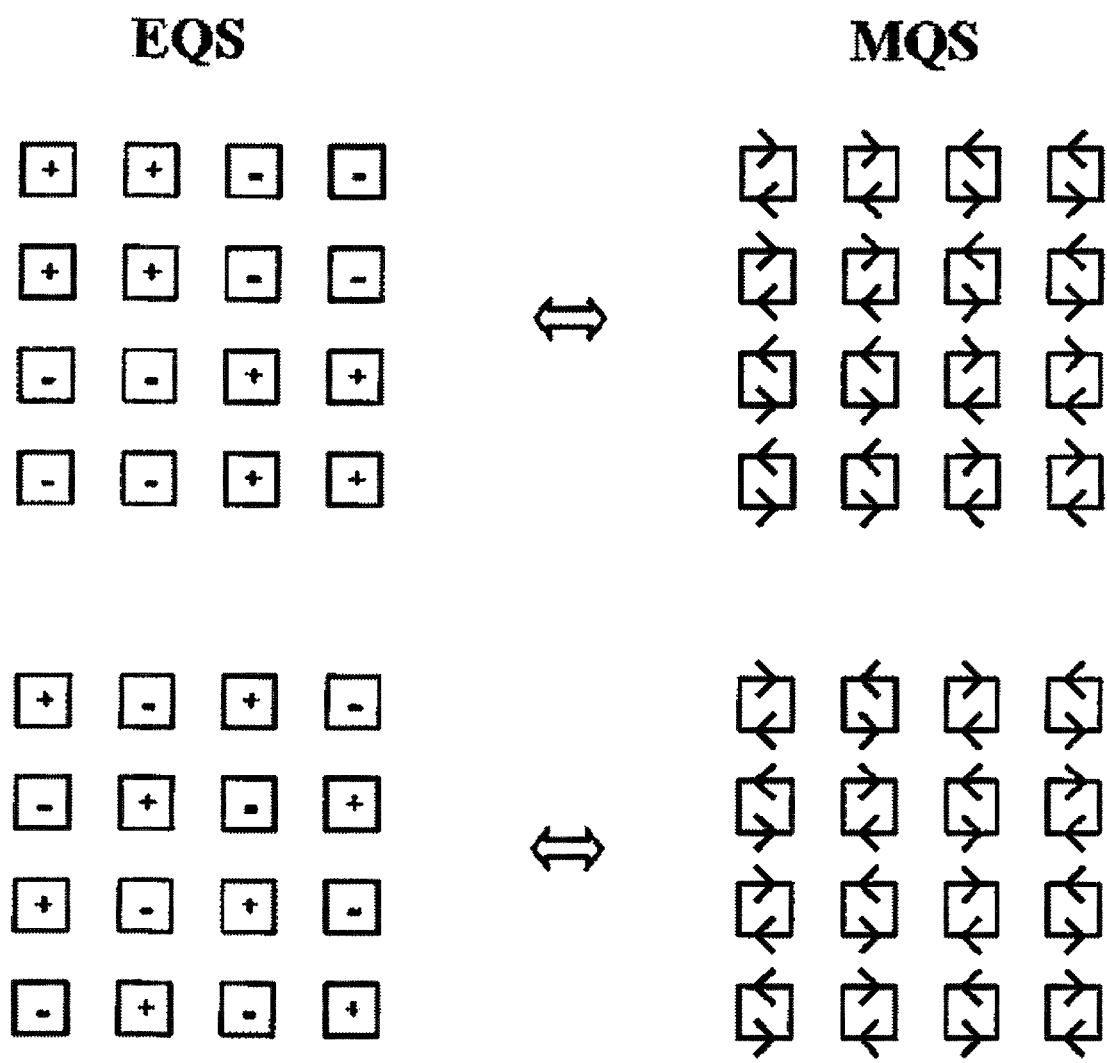
FIG. 29 is a schematic diagram illustrating excitation patterns.

As previously mentioned, there may be various excitation patterns for EQS sensor electrodes. The same applied to MQS sensor electrodes. The mapping from EQS to MQS is that the polarity of charge on an EQS sensor maps to the direction of current flow on an MQS sensor. A positive polarity EQS sensor is equivalent to an in-plane clockwise current on an MQS sensor, and a negative polarity EQS sensor is equivalent to an in-plane counterclockwise current on an MQS sensor. This is shown by the excitation patterns of FIG. 29, although it should be noted that such patterns are not limited to the example of FIG. 29.

Figure 30:
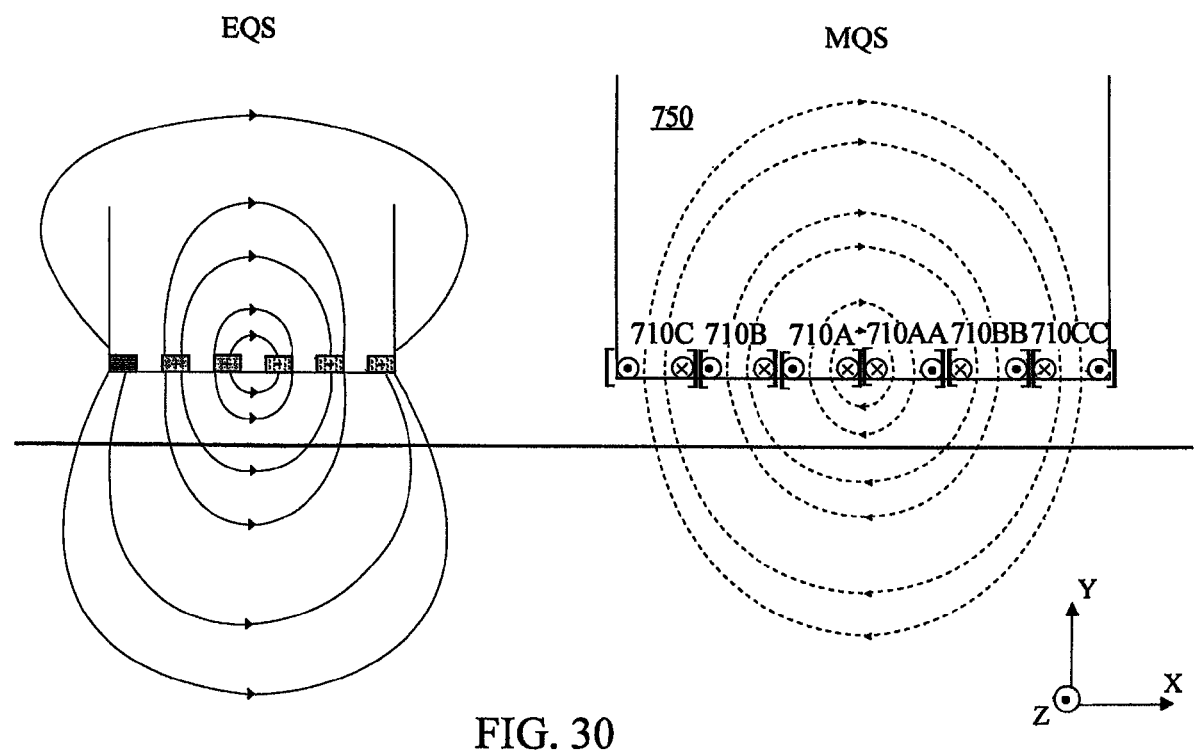
FIG. 30 is a schematic diagram illustrating one embodiment of a magnetic sensor head.

It was also previously mentioned that one can achieve multiple penetration depths into a sample by use of EQS sensor electrodes. The same applies to MQS sensor electrodes 710, as shown by FIG. 30, in addition to a confirming finite element simulation. FIG. 30 shows the MQS dual of an EQS sensor array. The direction of the current in the coils is chosen to match the polarity of the EQS sensor electrodes to achieve a similar field pattern. In addition, FIG. 30 illustrates the inherent dual-purpose of both guarding and sensing that coils serve when driven with a current at the same magnitude and phase as neighboring coils. Adjacent coils driven with currents of the same magnitude and phase act in the same way as guard electrodes driven with voltages of the same magnitude and phase.

FIG. 30 shows one embodiment of a magnetic sensor head above a sample. Each pair of "dot" and "cross" circles represent side views of individually addressable current loops that are MQS dual of an EQS electrode. The polarity of the "dot" and "cross" determine the direction of the electric field.

The windings in the embodiment are linear, and extend into the z-axis, forming a sensor head that is used to scan sideways. The sensor heads 750 could also be stacked in the z-axis to add a two-dimensional character to the sensor head 750, allowing one mechanical pass of the head to separately sense different parallel strips of the sample. This would increase the sensing rate.

FIG. 30 shows three pairs of windings labeled 710A and 710AA, 710B and 710BB, and 710C and 710CC; the members of each pair could be connected either in parallel or series so as to adjust their impedance to best match that of the drive electronics. Winding pair 710B and 710BB are the primary sense windings. The magnetic field lines linked by this pair penetrate deeply into the sample, and do not link fringing fields at the sides or center of the sensor head 750. Winding pairs 710A and 710AA, and 710C and 710CC, are guard windings, and link the fringing fields. The fringing fields add to the inductance of the winding pair yet do not give a focused view of the sample, so it is desirable for the sense windings not to link these field lines.

Figure 31:
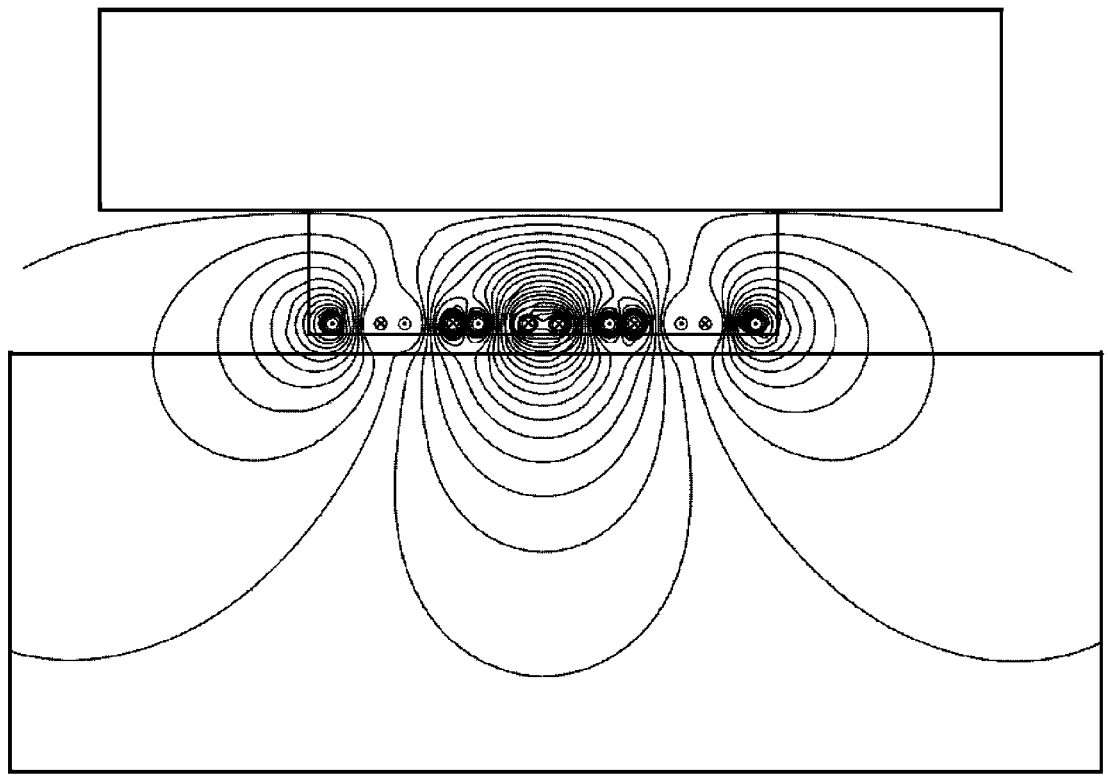
FIG. 31 is a schematic diagram illustrating an MQS analog to top-side guarding.
Figure 31:
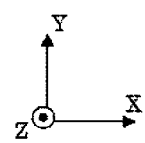

Herein, it has been described how guarding the top side of the EQS sensor electrodes is beneficial for shunting the fields through the sample. Shown in the schematic diagram of FIG. 31 is an MQS analog to top-side guarding (both a sketch and a finite element simulation for confirmation). A high-permeability, high-conductivity guard material is placed above the sensors. The highly conducting material prevents magnetic fields from penetrating its surface. Rather, the fields are forced to bend and flow tangentially along its surface. This acts as a top-side guard as it steers the fields, preventing them from fringing out to the top-side in the same way they fringe out on the bottom side. FIG. 31 illustrates how the fields do not stray above, but rather are confined to the area just below the top-side guard. Below the sensor array, the magnetic field lines are free to fringe out for feature/object detection.

Figure 32A:
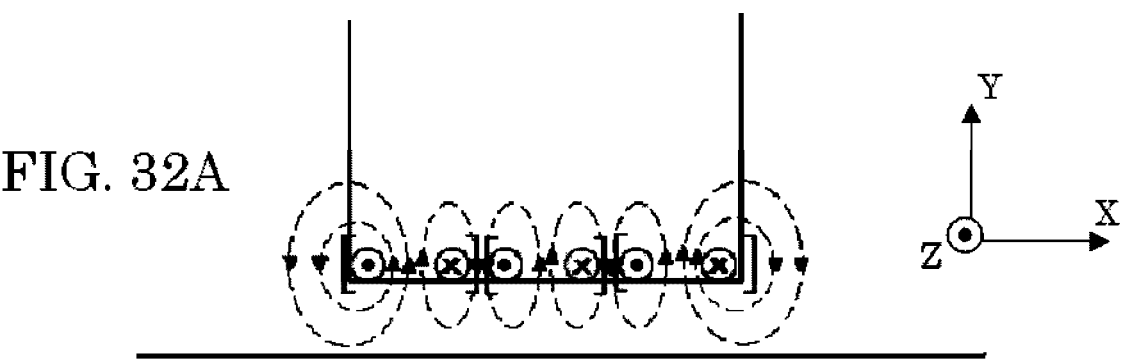
FIG. 32A and FIG. 32B are schematic diagrams illustrating alternative arrangements involving sense winding and guard windings.
Figure 32B:
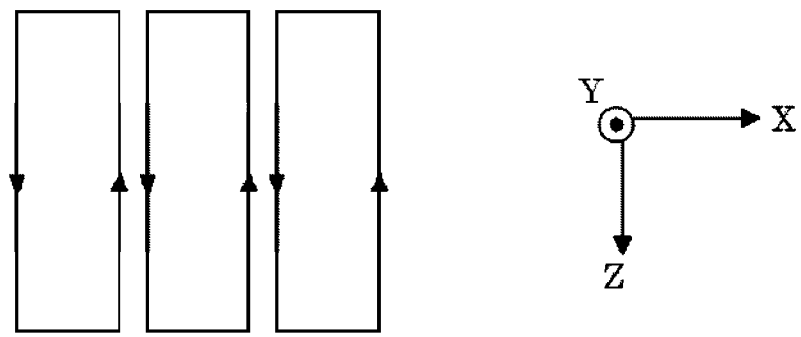

FIG. 32A and FIG. 32B show an alternative arrangement involving sense winding 800 and guard windings 802L and 802R. The current pattern in these windings is anti-symmetric, where as the current pattern in the windings in FIG. 30 is symmetric. As a consequence, the central guard winding is not necessary in FIG. 32, and the flux lines linked by sense winding 800 do not penetrate as deeply into the sample. Thus, this arrangement of windings and current offers an alternative view of the sample.

The electromagnetic imager is configured to have a spatially distributed array of electrodes or coils, wherein the electrodes are used for electroquasistatic imaging, and the coils are used for magnetoquasistatic imaging.

For example in the electrostatic imager, the electrode pixelated configuration could be arranged in a linear array of electrodes so as to form an electronic brush. This electronic brush is scanned across a surface to be imaged in a direction transverse to the linear array, so as to rapidly image a swath of surface, with each individual electrode imaging element (pixel) providing high spatial resolution along the length of the array and the scanning motion providing high resolution imaging in the direction of the scan, based upon choice of scan velocity and imaging bandwidth. During this motion, the pixelated sensor head is maintained at some desired distance, for example 50 nm to 100 nm, from the object surface via feedback control on sensor variables such as the electrode impedance or coil inductance, taken at single or multiple pixels, or averaged over some function of pixels, or via separate conventional sensing mechanisms such as a capacitance probe, inductance probe, optical interferometer, near field optical sensor, or vacuum gauge.

We can regard the individual electrodes as pixels on the sensor array, and thus a pixelated electrostatic sensor array is provided. Such pixellation is also applicable to arrays of coils for magnetoquasistatic sensor arrays, and thus the individual coil dimensions will define the magnetic pixel dimensions, and thus a pixelated magnetic sensor array is provided. In the following discussion, we focus on the electroquasistatic array. The extension to the magnetoquasistatic array can be made analogously to define an equivalent magnetic brush. Such a magnetic brush can be scanned and controlled for imaging in a manner analogous to the control and imaging of the electrostatic brush.

For rougher surfaces, or surfaces with significant curvature, the sensor spacing from the sample could be made larger, for example, 1000 nm. The desired pixel size can be chosen on the basis of intended spatial resolution and sensitivity. The electrode or coil arrays are typically driven at a high frequency, for example 1 GHz to 30 GHz in order to achieve high sensing bandwidth. It is desirable in many cases to achieve high sensing bandwidth to allow high imaging speed and productivity. This bandwidth can be electronically or digitally filtered to allow the selection of desired frequency content, for instance to filter out noise artifacts. This frequency can also be adjusted to allow sensing the sample properties at some desirable frequencies on the basis of, for example, electrical permittivity, conductivity, or magnetic permeability. The frequency of excitation can also be swept during a single pixel imaging process to create a spectral analysis of the surface electrical properties. This might be useful for instance to determine the material properties of the surface.

In an exemplary embodiment, a linear array could be composed of 10,000 electrode sets, each with sense and guard components, wherein the individual electrodes (pixels) could have dimensions of 100 nm by 100 nm on the face of the sensor. Thus the pixel dimensions are 100 nm by 100 nm in the imaging process. As a further example, if the electrodes have pixel dimensions of 50 nm by 50 nm, and are spaced with a linear pitch of 80 nm, then an array of 10,000 electrode sets will span a length of 800,000 nm or 0.8 mm. As this electronic brush is scanned in the transverse direction, an image of 10,000 pixels wide, equivalent to 0.8 mm width, is created during the scanning operation. If a data point is taken for each pixel during every 80 nm of transverse scan distance, then the image will be formed of image elements of 80 nm by 80 nm, over a width of 0.8 mm, and over the length of the transverse scan. Additional scans can then be performed in an adjacent fashion so as to cover the full surface of a sample to be imaged. For example, a successive scan can be performed at a spacing of 0.7 mm laterally from the previous scan. Measurements of lateral motion and scan motion, as well as image correlation algorithms can then be used to stitch together the successive scans in order to build up a full surface image. For example, with a 0.8 mm array width, 10,000 elements wide, and with 80 nm by 80 nm pixels, if the transverse scan velocity is 80 mm per second, then an imaging rate of 1,000,000 spatial samples per second can be achieved for each pixel. Over the lateral array width, this results in a total imaging rate of 10^10 pixels per second. With such a scan velocity, and with stitching together successive scans, a substrate of 80 mm by 80 mm could be imaged in about 100 successive scans, each scan pass requiring about 1 second scan time. Allowing time for the turnaround accelerations at the end of each scan, and for scan overlap, such a substrate could then be completely imaged with 80 nm by 80 nm resolution in a total scan time of about 200 seconds. Larger and smaller substrates would require correspondingly larger and smaller time to complete imaging, in proportion to the substrate area. Similar calculations apply to a linear array of magnetic sensing coils, and thus are applicable to a magnetic brush configuration.

The electronic brush configuration is primarily a line array for scanning laterally. Another embodiment uses a grid array of electrostatic or magnetic electrodes or coils to form a grid of imaging pixels, a grid pixelated array. Such a grid array can be used to image a substrate with all image elements acquired in parallel. This allows a faster imaging process of a given area of substrate. For example, an array of 1000 by 1000 electrode or coil pixels, with 100 nm spacing, can acquire an image of an area of 0.1 mm by 0.1 mm within a time on the order of 1, microsecond. Similarly, an array of 100,000 by 100,000 pixels with a 100 nm spacing can acquire an image of an area of 10 mm by 10 mm within about 1 microsecond.

Thus, multiple substrates can be scanned very rapidly. This would allow, for instance, the creation of very high-speed high-resolution image sequences (movies) of surfaces and samples of interest. For instance, it would be possible to visualize high-speed processes on a surface or substrate, for example, biological or chemical processes, forming or erosion of surface features, or other physical changes of interest. Such imaging would include internal features via field shaping of the array. A grid pixelated array could also be scanned over a surface to build up larger images, in a fashion analogous to the electronic or magnetic brush. Further, the pixel shapes can be adjusted to allow imaging of desired surface shapes with high image fidelity and resolution.

Arrays can similarly be fabricated on spherical, cylindrical or other non-planar surfaces in order to image samples with shapes other than planar, or to achieve other imaging characteristics. For example, the surface of a convex lens element could be scanned by an array fabricated on a concave surface. As another example, the linear array of an electronic brush could be fabricated on an arc in order to image a cylindrical surface, or to allow variable spacing from a planar surface.

It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention.

We claim:

1. An electromagnetic sensor for imaging in a sample, comprising:
    drive/sense electronics; and
    a pixelated sensor array having of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image,
    where in an active mode, at least a portion of the electrodes within the array of electrodes are individually drivable by independent voltage or current sources to excite the individual electrodes so as to allow for sample characterization at different penetration depths.

2. The sensor of claim 1, wherein the sensor further comprises a sensor head and associated electronics for interfacing with the pixelated sensor array and drive/sense electronics, and for transmitting the electrical properties of the electrodes to a computer for generation of the image.

3. The sensor of claim 2, wherein the computer further contains a first module for providing data acquisition from the sensor head and electronics, and a second module for signal inversion of data received from the pixelated sensor array.

4. The sensor of claim 1, wherein the electrodes are microfabricated on the same substrate as the drive/sense electronics.

5. The sensor of claim 1, wherein penetration depths are controlled by drive pattern.

6. The sensor of claim 1, wherein the array of electrodes is arranged as a linear array having sense and guard components, forming an electronic brush.

7. The sensor of claim 1, wherein the array of electrodes is arranged as a grid array having sense and guard components, forming an electronic brush.

8. The sensor of claim 1, wherein at least one of the sensor electrodes within the array of capacitive sensors is individually addressable and detectable.

9. The sensor of claim 1, wherein the electrodes are microfabricated.

10. An electromagnetic sensor for imaging a sample, comprising:
    drive/sense electronics; and
    a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image,
    wherein at least a portion of the electrodes within the array of electrodes are individually drivable by a drive frequency that is varied to enable sample spectral analysis.

11. A system for providing electromagnetic imaging through electroquasistatic sensing, comprising:
    drive/sense electronics;
    a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;
    a computer for providing data acquisition, and for providing signal inversion of data received from the pixelated sensor array; and
    a sensor head and associated electronics for interfacing with the pixelated sensor array and drive/sense electronics, and for transmitting the electrical properties of the electrodes to the computer for generation of the image,
    wherein at least a portion of the electrodes within the array of electrodes are individually drivable by a drive frequency that is varied to enable sample surface spectral analysis.

12. An electromagnetic sensor for imaging in a sample, comprising:
    drive/sense electronics; and
    a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image, wherein the array of electrodes is maintained a very small distance from a surface of the sample by use of a technique selected from the group consisting of implementing feedback position control via sensing capacitance from the sample, sensing currents relative to voltages of the capacitive sensor electrodes within the pixelated sensor array, and maintaining an average impedance over the pixelated sensor array constant in order to maintain the very small distance.

13. A system for providing electromagnetic imaging through electroquasistatic sensing, comprising:

drive/sense electronics;

a pixelated of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;

a computer for providing data acquisition, and for providing signal inversion of data received from the pixelated sensor array; and a sensor head and associated electronics for interfacing with the pixelated sensor array and drive/sense electronics, and for transmitting the electrical properties of the electrodes to the computer for generation of the image, wherein each electrode within the array of electrodes contains a face, wherein the face is the portion of the electrode that is positioned closest to the sample when the electromagnetic sensor is imaging the sample, wherein the face of each electrode is shaped so that the overall shape of the array of electrodes matches a surface of the sample that is to be imaged.

14. A system for providing electromagnetic imaging through electroquasistatic sensing, comprising:

drive/sense electronics;

a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;

a computer for providing data acquisition, and for providing signal inversion of data received from the pixelated sensor array; and a sensor head and associated electronics for interfacing with the pixelated sensor array and drive/sense electronics, and for transmitting the electrical properties of the electrodes to the computer for generation of the image, wherein at least one electrode within the array of electrodes does not have the same dimension as other electrodes within the array of electrodes, resulting in pixels having different shapes and/or sizes.

15. A system for providing electromagnetic imaging through electroquasistatic sensing, comprising:

drive/sense electronics;

a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;

a computer for providing data acquisition, and for providing signal inversion of data received from the pixelated sensor array; and a sensor head and associated electronics for interfacing with the pixelated sensor array and drive/sense electronics, and for transmitting the electrical properties of the electrodes to the computer for generation of the image, wherein the capacitive sensor electrodes are separated by a symmetry plane, where electrodes to a first side of the symmetry plane are driven by a first voltage and where electrodes to a second side of the symmetry plane are driven by a second voltage.

16. A system for providing electromagnetic imaging through electroquasistatic sensing, comprising:

drive/sense electronics;

a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;

a computer for providing data acquisition, and for providing signal inversion of data received from the pixelated sensor array; and a sensor head and associated electronics for interfacing with the pixelated sensor array and drive/sense electronics, and for transmitting the electrical properties of the electrodes to the computer for generation of the image, wherein the capacitive sensor electrodes are separated by a symmetry plane, where a first electrode located on a first side of the symmetry plane, is paired with a second electrode located on a second side of the symmetry plane, resulting in a first electrode pair, wherein the electroquasistatic fields that emanate from the first electrode pair is capable of penetrating the sample at a first depth based on the spacing between the first electrode and the second electrode.

17. The sensor of claim 16, wherein the array of capacitive sensor electrodes further comprises additional electrode pairs, wherein each pair of electrodes is capable of penetrating the sample at various depths based on its spacing and electroquasistatic fields that emanate from each pair.

18. The sensor of claim 17, wherein the electrode array is driven with a short spatial wavelength to limit a range of evanescent fields of the electrodes so as to allow the electromagnetic sensor to detect particles located on a surface of the sample.

19. A system for providing electromagnetic imaging through electroquasistatic sensing, comprising:

drive/sense electronics;

a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;

a computer for providing data acquisition, and for providing signal inversion of data received from the pixelated sensor array; and a sensor head and associated electronics for interfacing with the pixelated sensor array and drive/sense electronics, and for transmitting the electrical properties of the electrodes to the computer for generation of the image, wherein the array of capacitive sensor electrodes further comprises at least one guard electrode for concentrating the electroquasistatic fields in a direction so as to point the electroquasistatic fields toward the sample.

20. A system for providing electromagnetic imaging through electroquasistatic sensing, comprising:
    drive/sense electronics;
    a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;
    a computer for providing data acquisition, and for providing signal inversion of data received from the pixelated sensor array; and
    a sensor head and associated electronics for interfacing with the pixelated sensor array and drive/sense electronics, and for transmitting the electrical properties of the electrodes to the computer for generation of the image,
    wherein the array of capacitive sensors is used to detect a variation of properties of the sample and to predict dimensions and/or parameter values of the variation based upon a measured transimpedance between sensors within the array of capacitive sensors.

21. A system for providing electromagnetic imaging through electroquasistatic sensing, comprising:
    drive/sense electronics;
    a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;
    a computer for providing data acquisition, and for providing signal inversion of data received from the pixelated sensor array; and
    a sensor head and associated electronics for interfacing with the pixelated sensor array and drive/sense electronics, and for transmitting the electrical properties of the electrodes to the computer for generation of the image,
    wherein the array of capacitive sensor electrodes is arranged to provide a sensor array layout selected from the group consisting of a line array, a grid array, a guarded array, a coaxial/concentric array, a non-uniformly spaced array, and an array designed for locating specific features of the sample.

22. A system for providing electromagnetic imaging through electroquasistatic sensing, comprising:
    drive/sense electronics;
    a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;
    a computer for providing data acquisition, and for providing signal inversion of data received from the pixelated sensor array; and
    a sensor head and associated electronics for interfacing with the pixelated sensor array and drive/sense electronics, and for transmitting the electrical properties of the electrodes to the computer for generation of the image,
    wherein a variable frequency is used to drive the capacitive sensor electrodes to allow for investigation into frequency dependent properties of the sample for impedance spectral analysis.

23. A system for providing electromagnetic imaging through electroquasistatic sensing, comprising:
    drive/sense electronics;
    a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;
    a computer for providing data acquisition, and for providing signal inversion of data received from the pixelated sensor array; and
    a sensor head and associated electronics for interfacing with the pixelated sensor array and drive/sense electronics, and for transmitting the electrical properties of the electrodes to the computer for generation of the image,
    wherein the electromagnetic sensor is used for removing particles from the sample where the sample contains a flexible substrate, wherein the removal is made possible by the pixelated sensor array providing an electric field, forces of which cause the flexible substrate to deflect, and wherein the electric field forces are used to vibrate the flexible substrate resulting in removal of particles from the sample.

24. A system for providing electromagnetic imaging through electroquasistatic sensing, comprising:
    drive/sense electronics;
    a pixelated sensor array having an array of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;
    a computer for providing data acquisition, and for providing signal inversion of data received from the pixelated sensor array; and
    a sensor head and associated electronics for interfacing with the pixelated sensor array and drive/sense electronics, and for transmitting the electrical properties of the electrodes to the computer for generation of the image,
    wherein the capacitive sensor electrodes are arranged such that a first electrode is paired with a second electrode, resulting in a first electrode pair, wherein the electroquasistatic fields that emanate from the first electrode pair is capable of penetrating the sample at a first depth based on the spacing between the first electrode and the second electrode.

25. A system for providing electromagnetic imaging through electroquasistatic sensing, comprising:
    drive/sense electronics;
    a pixelated sensor array having an of capacitive sensor electrodes that source and/or sense electric fields that interact with the sample, and wherein the electrodes are individually drivable by the drive/sense electronics in a coordinated manner to establish a desired temporal and spatial pattern in which electrical properties of interaction between the electrodes and the sample are used to generate an image;

a computer for providing data acquisition, and for providing signal inversion of data received from the pixelated sensor array; and a sensor head and associated electronics for interfacing with the pixelated sensor array and drive/sense electronics, and for transmitting the electrical properties of the electrodes to the computer for generation of the image, wherein the electromagnetic sensor is used for removing particles from the sample, wherein the removal is made possible by the pixelated sensor array providing an electric field used to charge the particles to provide the particles with a net negative or net positive charge.

\* \* \* \* \*